US009486409B2

(12) United States Patent
Edelson et al.

(10) Patent No.: US 9,486,409 B2
(45) Date of Patent: Nov. 8, 2016

(54) PEPTIDE NANOPARTICLES AND USES THEREFOR

(71) Applicant: Anterios, Inc., New York, NY (US)

(72) Inventors: Jonathan Edelson, Scarsdale, NY (US); Timothy Kotyla, Natick, MA (US)

(73) Assignee: Anterios, Inc., New York, NY (US)

( * ) Notice: Subject to any disclaimer, the term of this patent is extended or adjusted under 35 U.S.C. 154(b) by 0 days.

(21) Appl. No.: 14/187,246

(22) Filed: Feb. 22, 2014

(65) Prior Publication Data

US 2014/0234382 A1  Aug. 21, 2014

Related U.S. Application Data

(63) Continuation of application No. 12/517,149, filed as application No. PCT/US2007/086040 on Nov. 30, 2007, now abandoned.

(60) Provisional application No. 60/872,206, filed on Dec. 1, 2006.

(51) Int. Cl.

| A61K 9/14 | (2006.01) |
|---|---|
| A61K 8/04 | (2006.01) |
| A61K 8/11 | (2006.01) |
| A61K 8/64 | (2006.01) |
| A61K 38/22 | (2006.01) |
| A61Q 1/06 | (2006.01) |
| A61Q 17/04 | (2006.01) |
| A61Q 19/08 | (2006.01) |
| B82Y 5/00 | (2011.01) |
| A61K 8/02 | (2006.01) |
| A61K 38/08 | (2006.01) |
| A61Q 19/00 | (2006.01) |

(52) U.S. Cl.
CPC ............... *A61K 9/14* (2013.01); *A61K 8/0241* (2013.01); *A61K 8/044* (2013.01); *A61K 8/11* (2013.01); *A61K 8/64* (2013.01); *A61K 38/08* (2013.01); *A61K 38/2207* (2013.01); *A61Q 1/06* (2013.01); *A61Q 17/04* (2013.01); *A61Q 19/00* (2013.01); *A61Q 19/08* (2013.01); *B82Y 5/00* (2013.01); *A61K 2800/413* (2013.01)

(58) Field of Classification Search
CPC ........................................................ A61K 9/14
See application file for complete search history.

(56) References Cited

U.S. PATENT DOCUMENTS

| 4,172,149 A | 10/1979 | Pinto et al. |
|---|---|---|
| 4,533,254 A | 8/1985 | Cook et al. |
| 4,908,154 A | 3/1990 | Cook et al. |
| 5,008,110 A | 4/1991 | Benecke et al. |
| 5,152,923 A | 10/1992 | Weder et al. |
| 5,374,614 A | 12/1994 | Behan et al. |
| 5,401,243 A | 3/1995 | Borodic |
| 5,502,045 A | 3/1996 | Miettinen et al. |
| 5,510,118 A | 4/1996 | Bosch et al. |
| 5,576,016 A | 11/1996 | Amselem et al. |
| 5,591,767 A | 1/1997 | Mohr et al. |
| 5,629,021 A | 5/1997 | Wright |
| 5,651,991 A | 7/1997 | Sugiyama et al. |
| 5,652,274 A | 7/1997 | Martin |
| 5,660,858 A | 8/1997 | Parikh et al. |
| 5,670,484 A | 9/1997 | Binder |
| 5,672,358 A | 9/1997 | Tabibi et al. |
| 5,683,712 A | 11/1997 | Cavazza |
| 5,753,241 A | 5/1998 | Ribier et al. |
| 5,766,605 A | 6/1998 | Sanders et al. |
| 5,851,452 A | 12/1998 | Vallet Mas et al. |
| 5,858,410 A | 1/1999 | Muller et al. |
| 5,925,341 A | 7/1999 | Cervantes et al. |
| 5,932,562 A | 8/1999 | Ostlund, Jr. |
| 5,948,433 A | 9/1999 | Burton et al. |
| 5,965,154 A | 10/1999 | Haralambopoulos |
| 5,994,414 A | 11/1999 | Franco et al. |
| 6,007,856 A | 12/1999 | Cox et al. |
| 6,010,715 A | 1/2000 | Wick et al. |
| 6,039,936 A | 3/2000 | Restle et al. |
| 6,165,500 A | 12/2000 | Cevc |
| 6,224,853 B1 | 5/2001 | Steel et al. |
| 6,265,180 B1 | 7/2001 | Zuelli et al. |
| 6,274,150 B1 | 8/2001 | Simonnet et al. |
| 6,312,708 B1 | 11/2001 | Donovan |
| 6,358,917 B1 | 3/2002 | Carruthers et al. |
| 6,387,411 B2 | 5/2002 | Bruce et al. |
| 6,429,189 B1 | 8/2002 | Borodic |

(Continued)

FOREIGN PATENT DOCUMENTS

| CA | 02067754 A1 | 2/1992 |
|---|---|---|
| CA | 2465123 A1 | 5/2003 |

(Continued)

OTHER PUBLICATIONS

Badea et al., In vivo cutaneous interferon-γ gene delivery using novel dicationic (gemini) surfactant-plasmid complexes, J Gene Medicine 7:1200-1214 (2005).
Bauerova et al., Chemical enhancers for transdermal drug transport, European J Drug Metabolism and Pharmacokinetics 26(1/2):85-94 (2001).
Bhartiya et al., Enhanced Wound Healing in Animal Models by Interferon and an Interferon Inducer, J Cell Physiol 150:312-319 (1992).
Bos and Meinardi, The 500 Dalton rule for the skin penetration of chemical compounds and drugs, Exp Dermatol 9:165-169 (2000).
Brewster, Delivering Anti-aging Actives, Cosmetics and Toiletries, 120(6):30, 32-34 (2005).
Chen et al., Transdermal protein delivery by a coadministered peptide identified via phage display, Nature Biotechnology 24(4):455-459 (2006).

(Continued)

*Primary Examiner* — Amber D Steele
(74) *Attorney, Agent, or Firm* — McCarter & English, LLP; Danielle L. Herritt, Esq.; Marcie B. Clarke

(57) ABSTRACT

The present invention provides nanoparticle compositions including one or more peptides. The present invention achieves transdermal delivery of such peptides without the need for peptide modification, or for use of chemical or mechanical abrasion or disruption of skin.

63 Claims, 1 Drawing Sheet

(56) References Cited

U.S. PATENT DOCUMENTS

| | | |
|---|---|---|
| 6,455,058 B1 | 9/2002 | Sun et al. |
| 6,558,941 B2 | 5/2003 | Zuelli et al. |
| 6,573,241 B1 | 6/2003 | Bigalke et al. |
| 6,589,588 B1 | 7/2003 | Wester et al. |
| 6,620,419 B1 | 9/2003 | Lintner |
| 6,623,780 B1 | 9/2003 | Stevens et al. |
| 6,632,440 B1 | 10/2003 | Quinn et al. |
| 6,670,322 B2 | 12/2003 | Goodnough et al. |
| 6,688,311 B2 | 2/2004 | Hanin |
| 6,720,001 B2 | 4/2004 | Chen et al. |
| 6,835,395 B1 | 12/2004 | Semple et al. |
| 6,835,895 B1 | 12/2004 | Asai et al. |
| 6,861,066 B2 | 3/2005 | Van de Casteele |
| 6,869,610 B2 | 3/2005 | Aoki et al. |
| 6,890,560 B2 | 5/2005 | Seo et al. |
| 6,902,737 B2 | 6/2005 | Quemin |
| 6,939,852 B2 | 9/2005 | Graham |
| 6,974,578 B1 | 12/2005 | Aoki et al. |
| 6,974,579 B2 | 12/2005 | Brin et al. |
| 7,001,602 B2 | 2/2006 | Schmidt |
| 7,226,605 B2 | 6/2007 | Suskind et al. |
| 7,228,259 B2 | 6/2007 | Freund |
| 7,255,865 B2 | 8/2007 | Walker |
| 7,384,918 B2 | 6/2008 | Graham |
| 7,419,996 B2 | 9/2008 | Chow et al. |
| 7,507,419 B2 | 3/2009 | Coleman, III |
| 7,763,663 B2 | 7/2010 | McCarthy et al. |
| 8,318,181 B2 | 11/2012 | Edelson et al. |
| 2002/0015721 A1 | 2/2002 | Slimonnet et al. |
| 2002/0048596 A1 | 4/2002 | Cevc |
| 2002/0098215 A1 | 7/2002 | Douin et al. |
| 2002/0107199 A1 | 8/2002 | Walker |
| 2002/0155084 A1 | 10/2002 | Roessler et al. |
| 2002/0165179 A1 | 11/2002 | Baker |
| 2003/0072801 A1 | 4/2003 | Curatolo et al. |
| 2003/0077240 A1 | 4/2003 | LeGrow et al. |
| 2003/0086888 A1 | 5/2003 | LeGrow et al. |
| 2003/0108597 A1 | 6/2003 | Chancellor et al. |
| 2003/0113349 A1 | 6/2003 | Coleman |
| 2003/0138465 A9 | 7/2003 | Douin et al. |
| 2003/0157138 A1 | 8/2003 | Eini et al. |
| 2003/0194412 A1 | 10/2003 | Baker et al. |
| 2003/0206955 A1 | 11/2003 | Sonneville-Aubrun et al. |
| 2003/0211140 A1 | 11/2003 | Mantripragada et al. |
| 2003/0224020 A1 | 12/2003 | Zabudkin et al. |
| 2004/0003324 A1 | 1/2004 | Uhlig et al. |
| 2004/0005370 A1 | 1/2004 | Breton |
| 2004/0009180 A1 | 1/2004 | Donovan |
| 2004/0009936 A1 | 1/2004 | Tang et al. |
| 2004/0028635 A1 | 2/2004 | Chauvierre et al. |
| 2004/0033202 A1 | 2/2004 | Cooper et al. |
| 2004/0033241 A1 | 2/2004 | Donovan |
| 2004/0037853 A1 | 2/2004 | Borodic |
| 2004/0048836 A1 | 3/2004 | Wilmott |
| 2004/0081688 A1 | 4/2004 | Del Curto et al. |
| 2004/0115159 A1 | 6/2004 | Tadlock et al. |
| 2004/0115727 A1 | 6/2004 | Steward et al. |
| 2004/0126397 A1 | 7/2004 | Aoki et al. |
| 2004/0127661 A1 | 7/2004 | Kaspar et al. |
| 2004/0132667 A1 | 7/2004 | Lintner |
| 2004/0151741 A1 | 8/2004 | Borodic |
| 2004/0191330 A1* | 9/2004 | Keefe et al. ............... 424/638 |
| 2004/0229038 A1 | 11/2004 | Cooper et al. |
| 2004/0258747 A1 | 12/2004 | Ponzoni et al. |
| 2004/0258758 A1 | 12/2004 | Gustow et al. |
| 2005/0038096 A1 | 2/2005 | Chow et al. |
| 2005/0048088 A1 | 3/2005 | Zulli et al. |
| 2005/0065090 A1 | 3/2005 | Ludin et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0079228 A1 | 4/2005 | Jaiswal et al. |
| 2005/0096340 A1 | 5/2005 | Zhang et al. |
| 2005/0118254 A1 | 6/2005 | Choi et al. |
| 2005/0123897 A1 | 6/2005 | Cevc et al. |
| 2005/0124378 A1 | 6/2005 | Griffith et al. |
| 2005/0136024 A1 | 6/2005 | Stockel |
| 2005/0142150 A1 | 6/2005 | Graham |
| 2005/0147688 A1 | 7/2005 | Russell |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0208083 A1 | 9/2005 | Annis |
| 2005/0214325 A1 | 9/2005 | David |
| 2005/0214378 A1* | 9/2005 | Hoarau et al. ............... 424/490 |
| 2005/0226842 A1 | 10/2005 | Douin et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0073208 A1 | 4/2006 | First |
| 2006/0084353 A1 | 4/2006 | Wong et al. |
| 2006/0093624 A1 | 5/2006 | Graham |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0182794 A1 | 8/2006 | Modi |
| 2006/0188525 A1 | 8/2006 | Donovan |
| 2007/0009555 A1 | 1/2007 | Borodic |
| 2007/0036831 A1 | 2/2007 | Baker |
| 2007/0104743 A1 | 5/2007 | Lehtola et al. |
| 2007/0116723 A1 | 5/2007 | Coleman |
| 2007/0148194 A1 | 6/2007 | Amiji et al. |
| 2007/0178121 A1 | 8/2007 | First et al. |
| 2007/0253911 A1 | 11/2007 | Tamarkin et al. |
| 2007/0292359 A1 | 12/2007 | Friedman et al. |
| 2008/0050352 A1 | 2/2008 | Webb et al. |
| 2008/0206155 A1 | 8/2008 | Tamarkin et al. |
| 2008/0207737 A1 | 8/2008 | Zinger |
| 2008/0274195 A1 | 11/2008 | Nicolosi et al. |
| 2009/0041680 A1 | 2/2009 | Tamarkin et al. |
| 2009/0306198 A1 | 12/2009 | Nicolosi et al. |
| 2010/0040883 A1 | 2/2010 | McCarthy et al. |
| 2010/0137357 A1 | 6/2010 | Koleng et al. |
| 2010/0150994 A1 | 6/2010 | Kotyla |
| 2010/0172943 A1 | 7/2010 | Edelson et al. |
| 2010/0183726 A1 | 7/2010 | Nicolosi et al. |
| 2010/0233251 A1 | 9/2010 | Von Andrian et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2011/0212157 A1 | 9/2011 | Edelson et al. |
| 2012/0164182 A1 | 6/2012 | Edelson et al. |
| 2012/0328525 A1 | 12/2012 | Edelson et al. |
| 2012/0328549 A1 | 12/2012 | Edelson et al. |
| 2012/0328701 A1 | 12/2012 | Edelson et al. |

FOREIGN PATENT DOCUMENTS

| | | |
|---|---|---|
| CA | 2543722 A1 | 5/2005 |
| CA | 2554052 A1 | 8/2005 |
| CA | 2494473 C | 6/2007 |
| CA | 2631927 A1 | 4/2008 |
| CA | 2688415 A1 | 12/2008 |
| DE | 102004016710 A1 | 10/2005 |
| DE | 102006046076 A1 | 4/2007 |
| EP | 0315079 A1 | 5/1989 |
| EP | 0406162 A2 | 1/1991 |
| EP | 0572080 B1 | 11/1995 |
| EP | 0753311 A1 | 1/1997 |
| EP | 1080720 A1 | 3/2001 |
| EP | 0770422 B1 | 9/2002 |
| EP | 1430906 A2 | 6/2004 |
| EP | 1586336 A1 | 10/2005 |
| EP | 1652515 A1 | 5/2006 |
| EP | 1249232 B1 | 10/2006 |
| EP | 1784163 A1 | 5/2007 |
| EP | 1345597 B1 | 10/2007 |
| FR | 2849375 A1 | 7/2004 |
| JP | 1990000203 | 1/1990 |
| JP | 1995285863 | 10/1995 |
| JP | 1996507515 | 8/1996 |
| JP | 2001513331 A | 9/2001 |

(56) References Cited

FOREIGN PATENT DOCUMENTS

| | | |
|---|---|---|
| JP | 2002308728 A | 10/2002 |
| JP | 2003527411 A | 9/2003 |
| JP | 2004519447 A | 7/2004 |
| JP | 2006199589 A | 8/2006 |
| JP | 2006273821 A | 10/2006 |
| KR | 10-2004-0062602 A | 7/2004 |
| WO | WO-9011364 A1 | 10/1990 |
| WO | WO-9318752 A1 | 9/1993 |
| WO | WO-9420072 A1 | 9/1994 |
| WO | WO-9522973 A1 | 8/1995 |
| WO | WO-9535157 A1 | 12/1995 |
| WO | WO-98/51278 A2 | 11/1998 |
| WO | WO-9907238 A2 | 2/1999 |
| WO | WO-9944594 A1 | 9/1999 |
| WO | WO-0007621 A2 | 2/2000 |
| WO | WO-0038653 A1 | 7/2000 |
| WO | WO-0110413 A2 | 2/2001 |
| WO | WO-0170197 A2 | 9/2001 |
| WO | WO-0188019 A1 | 11/2001 |
| WO | WO-0239979 A1 | 5/2002 |
| WO | WO 02/051390 * 7/2002 ............... A61K 9/51 | |
| WO | WO-02051390 A2 | 7/2002 |
| WO | WO-02056866 A1 | 7/2002 |
| WO | WO-02080864 A1 | 10/2002 |
| WO | WO-03000243 A1 | 1/2003 |
| WO | WO-03011333 A1 | 2/2003 |
| WO | WO-03037933 A2 | 5/2003 |
| WO | WO-03092585 A2 | 11/2003 |
| WO | WO-03101483 A1 | 12/2003 |
| WO | WO-2004006954 A2 | 1/2004 |
| WO | WO-2004076634 A2 | 9/2004 |
| WO | WO-2004084839 A2 | 10/2004 |
| WO | WO-2005013938 A1 | 2/2005 |
| WO | WO-2005020962 A1 | 3/2005 |
| WO | WO-2005023282 A1 | 3/2005 |
| WO | WO-2005027872 A2 | 3/2005 |
| WO | WO-2005042539 A1 | 5/2005 |
| WO | WO-2005058370 A1 | 6/2005 |
| WO | WO-2005063377 A1 | 7/2005 |
| WO | WO-2005070394 A2 | 8/2005 |
| WO | WO-2005082514 A2 | 9/2005 |
| WO | WO-2005084361 A2 | 9/2005 |
| WO | WO-2005102285 A1 | 11/2005 |
| WO | WO-2006005910 A2 | 1/2006 |
| WO | WO-2006028339 A1 | 3/2006 |
| WO | WO-2006050926 A2 | 5/2006 |
| WO | WO-2006084353 A1 | 8/2006 |
| WO | WO-2006094263 A2 | 9/2006 |
| WO | WO-2006138127 A2 | 12/2006 |
| WO | WO-2007041664 A1 | 4/2007 |
| WO | WO-2007046102 A2 | 4/2007 |
| WO | WO-2007089454 A2 | 8/2007 |
| WO | WO-2007103555 A2 | 9/2007 |
| WO | WO-2007149868 A2 | 12/2007 |
| WO | WO-2008010788 A2 | 1/2008 |
| WO | WO-2008038147 A2 | 4/2008 |
| WO | WO-2008045107 A2 | 4/2008 |
| WO | WO-2008070538 A2 | 6/2008 |
| WO | WO-2008077641 A1 | 7/2008 |
| WO | WO-2008140594 A2 | 11/2008 |
| WO | WO-2008151022 A2 | 12/2008 |
| WO | WO-2009158687 A1 | 12/2009 |
| WO | WO-2010087964 A2 | 8/2010 |

OTHER PUBLICATIONS

Choi et al, Percutaneous Absorption, Fourth Edition Bronaugh and Maibach ed., Taylor and Francis, Boca Ratonm Florida, Index and Table of contents only 155:33 (2005).
Cocconi et al., Treatment of Metastatic Malignant Melanoma with Dacarbazine Plux Tamoxifen, New England J Medicine 327(8):516-23 (1992).
Croda Inc., Pharmaceutical Technology, 3 pages (2005), Retrieved online: http://www.pharmtech.com/pharmtech/Corporate=Capabilities/Croda-Inc/ArticleStandard/Article/detail/399061.
Dalgleish et al., The characterization of small emulsion droplets made from milk proteins and triglyceride oil, Colloids and Surfaces, 123-124:145-153 (May 15, 1997).
De Campo et al., Five-component food-grade microemulsions: Structural characterization by SANS, J Colloid and Interface Science, 274:251-267 (2004).
De Paiva and Dolly, Light chain of botulinum nerotoxin is active in mammalian motor nerve terminals when delivered via liposomes, FEBS 277(1,2):171-174 (1990).
Delgado-Charro et al., Delivery of a hydrophilic solute through the skin from novel microemulsion systems, Eur J Pharmaceutics and Biopharmaceutics 43[1]:37-42 (1997).
Examination Report for EP 07874325.9, 8 pages (Apr. 5, 2012).
Examination Report for SG 200903663-3, 4 pages (Oct. 11, 2011).
Extended European Search Report for EP 12160402.9, 4 pages (Aug. 6, 2012).
Helene et al., Control of Gene Expression by Triple Helix-Forming Oligonucleotides, Ann N.Y. Acad Sci 660:27-36 (1992).
Helene, The anti-gene strategy: control of gene expression by triplex-forming-oligonucleotides, Anti-Cancer Drug Des 6:569-584 (1991).
Hickerson et al., SiRNA-Mediated Selective Inhibition of Mutant Keratin mRNAs Responsible for the Skin Disorder Pachyonychia Congenita, Ann. N.Y. Acad. Sci. 1082:56-61 (2006).
International Preliminary Report on Patentability for PCT/US2006/035343, 5 pages (Mar. 18, 2008).
International Preliminary Report on Patentability for PCT/US2007/086018, 7 pages (Jun. 3, 2009).
International Preliminary Report on Patentability for PCT/US2007/086040, 13 pages (Feb. 16, 2010).
International Preliminary Report on Patentability for PCT/US2008/065329, 8 pages (Dec. 1, 2009).
International Preliminary Report on Patentability for PCT/US2009/048972, 6 pages (Jan. 5, 2011).
International Preliminary Report on Patentability for PCT/US2012/022276, 10 pages (Aug. 8, 2013).
International Preliminary Report on Patentability for PCT/US2012/022277, 7 pages (Aug. 8, 2013).
International Preliminary Report on Patentability for PCT/US2012/022278, 8 pages (Aug. 8, 2013).
International Preliminary Report on Patentability for PCT/US2012/022279, 9 pages (Aug. 8, 2013).
International Preliminary Report on Patentability for PCT/US2012/022280, 8 pages (Aug. 8, 2013).
International Preliminary Report on Patentability for PCT/US2012/022281, 7 pages (Aug. 8, 2013).
International Search Report for PCT/US2006/026918, 4 pages (Jun. 19, 2008).
International Search Report for PCT/US2006/035343, 1 page (Aug. 15, 2007).
International Search Report for PCT/US2006/046236, 3 pages (Jun. 17, 2008).
International Search Report for PCT/US2007/086018, 5 pages (Sep. 17, 2008).
International Search Report for PCT/US2007/086040, 7 pages (Feb. 9, 2010).
International Search Report for PCT/US2008/065329, 5 pages (Mar. 12, 2009).
International Search Report for PCT/US2009/048972, 5 pages (Dec. 1, 2009).
International Search Report for PCT/US2012/022276, 6 pages (Jul. 19, 2012).
International Search Report for PCT/US2012/022277, 4 pages (Jul. 6, 2012).
International Search Report for PCT/US2012/022278, 4 pages (Mar. 23, 2012).
International Search Report for PCT/US2012/022279, 7 pages (Nov. 29, 2012).
International Search Report for PCT/US2012/022280, 4 pages (Apr. 27, 2012).

(56) References Cited

OTHER PUBLICATIONS

International Search Report for PCT/US2012/022281, 4 pages (Apr. 24, 2012).
Izquierdo et al., The influence of surfactant mixing ration on nano-emulsion formation by the pit method, J Colloid and Interface Sci. 285:388-394 (2004).
Kakumanu et al., A Nanoemulsion Formulation of Dacarbazine Reduces Tumor Size in a Xenograft Mouse Epidermoid Carcinoma Model Compared to Dacarbazine Suspension, Nanomedicine: NBM 7(3):277-283 (2011).
Katayama et al., A Pentapeptide from Type I Procollagen Promotes Extracellular Matrix Production, J Biol Chem 268(14):9941-9944 (1993).
Keen et al., Botulinum Toxin A for Hyperkinetic Facial Lines: Results of a Double-Blind, Placebo-Controlled Study, Plastic and Reconstructive Surgery, 94(1):94-9 (1994).
Kitson, Drugs Used for Skin Diseases, Published in Dermatologic, Cosmeceutic, and Cosmetic Development Therapeutic and Novel Approaches, Ed Walters and Roberts 11-20 (2008).
Kotyla et al., Increased bioavailability of a transdermal application of a nano-sized emulsion preparation, International Journal of Pharmaceutics 347:144-148 (2008).
Kronberg et al., Preparation and Evaluation of Sterically Stabilized Liposomes: Colloidal Stability, Serum Stability, Macrophage Uptake, and Toxicity, J Pharmaceutical Sciences 79(8):667-671 (1990).
Kuo et al., Nanomulsions of an Anti-Oxidant Synergy Formulation Containing Gamma Tocopherol Have Enhanced Bioavailability and Anti-Inflammatory Properties, Int'l J Pharmaceutics 363:206-213 (2008).
Lin et al., Delivery of plasmid DNA expression vector for keratinocyte growth factor-1 using electroporation to improve cutaneous wound healing in a septic rat model, Wound Repair and Regenertion 14:618-624 (2006).
Ludewig and Hoffmann, Adoptive Immunotherapy Methods and Protocols, Humana Press Inc., NJ 393 (2005).
Lupo, Cosmeceutical Peptides, Dermatologic Surgery 31:832-836 (2005).
Maher, DNA Triple-Helix Formation: An Approach to Artificial Gene Repressors?, BioEssays 14:807-815 (1992).
Montecucco et al., Effect of pH on the interaction of botulinum neurotoxins A, B and E with liposomes, Biochem J 259:47-53 (1989).
Morel et al., Incorporation in lipospheres of {D-Trp-6}LHRH, Int'l J Pharmaceutics 105(2):R01-R03 (1994).
Muller, R.H. et al., Solid lipid nanoparticles (SLN) for controlled drug delivery—a review of the state of the art. European Journal of Pharmaceutics and Biopharmaceutics, 50(1):161-77 (2000).
Poste et al., Lipid Vesicles as Carriers for Introducing Biologically Active Materials into Cells, Methods in cell biology 14:34-35 (1976).
PTO892 mailed Dec. 11, 2012, 1 page.
PTO892, 1 page (Feb. 19, 2013).
Robinson, et al., Topical palmitoyl pentapeptide provides improvement in photoaged human facial skin, Int'l J Cosmetic Science 24:155-160 (2005).
Santiago et al., Topical Application of a Peptide Inhibitor of Transforming Growth Factor-β1 Ameliorates Bleomycin-Induced Skin Fibrosis, J Investigative Dermatorlogy 125:450-455 (2005).
Sarver et al., Ribozymes as Potential Anti-HIV-1 Therapeutic Agents, Science 247:1222-1225 (1990).
Schmalfuβ et al., Modification of drug penetration into human skin using microemulsions, J Controlled Release 46(3):279-285 (1997).
Search Report for AU2007329579, 3 pages (Jun. 1, 2012).
Search Report for AU2007353340, 2 pages (May 28, 2012).
Search Report for SG 200903662-5, 8 pages (Oct. 29, 2010).
Search Report for SG 200903663-3, 8 pages (Oct. 12, 2010).
Shone et al., A 50-kDa fragment from the $NH_2$-terminus of the heavy subunit of *Clostridium botulinum* type A neurotoxin forms channels in lipid vesicles, Eur J Biochem 167:175-180 (1987).
Supplementary European Search Report for Application No. EP06851782, 10 pages, dated Jul. 3, 2012.
Supplementary European Search Report for EP06851414.0, 8 pages (Oct. 1, 2012).
Tadros et al., Formation and stability of nano-emulsions, Advances in Colloid and Interface Science 108:109-303-318 (2004).
Tagne et al., Nanoemulsion Preparations of the Anticancer Drug Dacarbazine Significantly Increase Its Efficacy in Xenograft Mouse Melanoma Model, Molecular Pharmaceutics 5(6):1055-1063 (2008).
Trotta et al., Elastic Liposomes for Skin Delivery of Dipotassium Glycyrrhizinate, Int'l J Pharmaceutics 241:319-327 (2002).
Verma et al., Particle size of liposomes influences dermal delivery of substances into skin, Int'l J Pharmaceutics 141-151 (2003).
Wang et al., Enhancing effect of Labrafac Lipophile WL 1349 on oral bioavailability of hydroxysafflor yellow A in rats, International Journal of Pharmaceutics 358:198-204 (2008).
Written Opinion for PCT/US2007/086018, 6 pages (Sep. 17, 2008).
Written Opinion for PCT/US2007/086040, 12 pages (Feb. 9, 2010).
Written Opinion for PCT/US2008/065329, 7 pages (Mar. 12, 2009).
Written Opinion for PCT/US2009/048972, 5 pages (Dec. 1, 2009).
Written Opinion for PCT/US2012/022276, 9 pages (Jul. 19, 2012).
Written Opinion for PCT/US2012/022277, 6 pages (Jul. 6, 2012).
Written Opinion for PCT/US2012/022279, 7 pages (Nov. 29, 2012).
Written Opinion for PCT/US2012/022280, 7 pages (Apr. 27, 2012).
Written Opinion for PCT/US2012/022281, 6 pages (Apr. 24, 2012).
Written Opinion for PCT/US20120/22278, 7 pages (Mar. 23, 2012).
Written Opinion for SG 200903663-3, 7 pages (Oct. 12, 2010).
Written Opinion for SG 201009039-7, 6 pages (Mar. 12, 2012).
Written Opinion for SG200903662-5, 4 pages (Oct. 29, 2010).
Wu et al., Topical Transfection Using Plasmid DNA in a Water-in-Oil Nanoemulsion, Int J Pharmceutics 221(1/02):23-34 (2001).
Wu et al., Topical Transport of Hydrophilic Compounds Using Water-in-Oil Nanoemulsions, Int. J. Pharmaceutics, 220:63-75 (2001).
Barr et al., Different Substrate Recognition Requirements for cleavage of Synaptobrevin-2 by Clostridium baratii and Clostridium botulinum, Applied and Environmental Microbiology p. 1301-1308, 2011.

\* cited by examiner

AA Control Group Example, 400x, Masson's Trichrome, Score 2/4.
BB Treatment Group Example, 400x, Masson's Trichrome, Score 4/4.

AA Exemple de groupe témoin, 400x, trichrome de Masson, score 2/4
BB Exemple de groupe de traitement, 400x, trichrome de Masson, score 4/4

PEPTIDE NANOPARTICLES AND USES THEREFOR

RELATED APPLICATIONS

This is a Continuation of co-pending U.S. patent application Ser. No. 12/517,149, filed Mar. 1, 2010, which is a 35 U.S.C. §371 National Stage of International Application No. PCT/US07/86040, entitled "PEPTIDE NANOPARTICLES AND USES THEREFOR" filed Nov. 30, 2007, which claims the benefit of and priority to U.S. Provisional Application No. 60/872,206, filed Dec. 1, 2006, the contents of each of which are hereby incorporated by reference in their entirety.

SEQUENCE LISTING

In accordance with 37 C.F.R. §1.52(e)(5), a Sequence Listing in the form of a text file (entitled "Sequence_Listing," created on Apr. 11, 2014 and 4 kilobytes) is incorporated herein by reference in its entirety.

BACKGROUND OF THE INVENTION

Peptides have been shown to have beneficial cosmetic and therapeutic effects on the skin. In experimental models, short peptides (of length up to 30 amino acids) have been shown to stimulate collagen growth in the extra-cellular matrix of the skin, which may improve the appearance of skin as well as improve the healing of damaged skin (Katayama, et al., 1993, *J. Biol. Chem.*, 268:9941; incorporated herein by reference). Modified peptides have also been shown to decrease the appearance of wrinkles through the modulation of enzymes that influence muscular contractions in the muscles underlying the skin that contribute to wrinkle formation (Lupo, 2005, *Dermatol. Surg.*, 31:832; incorporated herein by reference).

However, a major problem in achieving the potential cosmetic and therapeutic effects of these peptides in humans has been the transdermal delivery of the peptides across the outer skin barrier (stratum corneum) to the site of biological action, e.g., the extra-cellular matrix or underlying muscle (Robinson, et al., 2005, *International J. Cosmetic Science* 27:155; incorporated herein by reference). To achieve the delivery of transdermal delivery of the peptides in humans, the peptides have had to be chemically modified by the addition of chemical moieties such as but not limited to acetyl and/or palmitoyl groups (Robinson, et al., supra). These chemical modifications are disadvantageous because they are expensive and time-consuming, which negatively impact the commercial manufacture of a product containing these peptides. Chemical modifications of the peptides can also decrease the biological activity of the peptide by decreasing its ability to bind at the cellular receptor site of biological activity (through, for example, steric interference), thus making it less effective. A peptide that is less effective biologically would be less effective for cosmetic or therapeutic purposes. Comparably, a peptide that is less effective biologically would need to be administered at higher levels to achieve its desired biological effect (if the effect were even possible), which would be a cost disadvantage for the commercial manufacture of a product.

SUMMARY OF THE INVENTION

The present invention describes nanoparticles that incorporate unmodified short peptides (2 to 30 amino acids long) that are biologically active agents in the skin (including epidermis and dermis), sub-cutaneous tissue (including adipose tissue), and contiguous muscles.

Inventive nanoparticles can be applied to the skin of a subject. In some embodiments, inventive nanoparticles achieve transdermal delivery of incorporated peptides to the subject.

Inventive nanoparticles can be applied to the skin as a simple suspension or dispersion or mixed with one or more excipients and prepared as a formulation such as, but not limited to, a skin softener, nutrition lotion, cleansing lotion, cleansing cream, skin milk, emollient lotion, massage cream, emollient cream, make-up base, lipstick, facial pack or facial gel, cleaner formulation (e.g. shampoos, rinses, body cleanser, hair-tonics, and soaps), and dermatological composition (e.g. lotions, ointments, gels, creams, patches and sprays).

Thus, the present invention provides systems and compositions for the transdermal delivery of unmodified peptides. Among the many advantages of this invention is the ability to delivery peptides without injection and further without a requirement for mechanical or chemical abrasion or alteration of skin. Additional advantages include an ability to utilize unmodified peptides, thereby simplifying and reducing the cost of production of inventive cosmetic and/or pharmaceutical preparations and, further, preserving biological activity of the peptide.

DEFINITIONS

Figure 1:
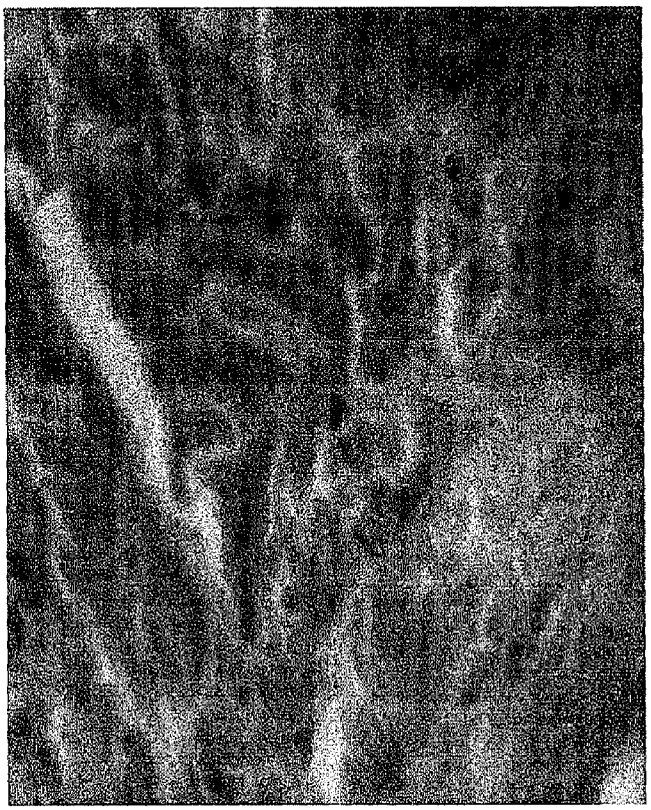
FIG. 1. Histological Analysis of Mice Treated with Peptide Nanoparticles. Shown are photomicrographs of skin tissue stained with Masson's Trichrome stain. The average histologic score was 2.33 out of a possible 4 in the Control Group (nanoparticle formulation without pentapeptide). The average histologic score was 3.67 out of a possible 4 in the Treatment Group (nanoparticle formulation with pentapeptide).

Abrasion: The term "abrasion," as used herein refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g. magnesium or aluminum particles), acids (e.g. alpha-hydroxy acids or beta-hydroxy acids), alcohols, may cause abrasion. In general, permeation enhancers such as those described, for example, by Donovan (e.g., U.S. Patent Publications 2004/009180 and 2005/175636 and PCT Publication WO 04/06954; all of which are incorporated herein by reference), and Graham (e.g., U.S. Pat. No. 6,939,852 and U.S. Patent Publication 2006/093624; both of which are incorporated herein by reference), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. Amino acids, including carboxy- and/or amino-terminal amino acids in peptides, can be modified by methylation, amidation, acetylation, and/or substitution with other chemical groups that can change the peptide's circulating half-life without adversely affecting their activity. However, as described herein, the present invention is specifically directed to "unmodified peptides", meaning peptides that have not been chemically modified in order to facilitate or achieve transdermal delivery. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active agent: As used herein, the phrase "biologically active agent" refers to any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Botulinum toxin: The term "botulinum toxin," as used herein, refers to any neurotoxin produced by *Clostridium botulinum*. Except as otherwise indicated, the term encompasses fragments or portions (e.g., the light chain and/or the heavy chain) of such neurotoxin that retain appropriate activity (e.g., muscle relaxant activity). The phrase "botulinum toxin," as used herein, encompasses the botulinum toxin serotypes A, B, C, D, E, F, and G. Botulinum toxin, as used herein, also encompasses both a botulinum toxin complex (i.e., for example, the 300, 600, and 900 kD complexes) as well as the purified (i.e., for example, isolated) botulinum toxin (i.e., for example, about 150 kD). "Purified botulinum toxin" is defined as a botulinum toxin that is isolated, or substantially isolated, from other proteins, including protein that for a botulinum toxin complex. A purified toxin may be greater than 95% pure, and preferably is greater than 99% pure. Those of ordinary skill in the art will appreciate that the present invention is not limited to any particular source of botulinum toxin. For example, botulinum toxin for use in accordance with the present invention may be isolated from *Clostridium botulinum*, may be chemically synthesized, may be produced recombinantly (i.e., in a host cell or organism other than *Clostridium botulinum*), etc.

Characteristic portion: As used herein, the phrase a "characteristic portion" of a substance, in the broadest sense, is one that shares some degree of sequence and/or structural identity and/or at least one functional characteristic with the relevant intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally will contain at least 2, 5, 10, 15, 20 or more amino acids. In general, a characteristic portion is one that, in addition to the sequence identity specified above, shares at least one functional characteristic with the relevant intact protein. In some embodiments, the characteristic portion may be biologically active.

Hydrophilic: As used herein, a "hydrophilic" substance is a substance that may be soluble in polar solvents. In some embodiments, a hydrophilic substance can transiently bond with polar solvents. In some embodiments, a hydrophilic substance transiently bonds with polar solvents through hydrogen bonding. In some embodiments, the polar solvent is water. In some embodiments, a hydrophilic substance may be ionic. In some embodiments, a hydrophilic substance may be non-ionic. In some embodiments, a hydrophilic substance may dissolve more readily in water, polar solvents, or hydrophilic solvents than in oil, non-polar solvents, or hydrophobic solvents. In some embodiments, a hydrophilic substance may dissolve less readily in oil, non-polar solvents, or hydrophobic solvents than in water, polar solvents, or hydrophilic solvents. In some embodiments, a substance is hydrophilic relative to another substance because it is more soluble in water, polar solvents, or hydrophilic solvents than is the other substance. In some embodiments, a substance is hydrophilic relative to another substance because it is less soluble in oil, non-polar solvents, or hydrophobic solvents than is the other substance.

Hydrophobic: As used herein, a "hydrophobic" substance is a substance that may be soluble in non-polar solvents. In some embodiments, a hydrophobic substance is repelled from polar solvents. In some embodiments, the polar solvent is water. In some embodiments, hydrophobic substances are non-polar. In some embodiments, a hydrophobic substance may dissolve more readily in oil, non-polar solvents, or hydrophobic solvents than in water, polar solvents, or hydrophilic solvents. In some embodiments, a hydrophobic substance may dissolve less readily in water, polar solvents, or hydrophilic solvents than in oil, non-polar solvents, or hydrophobic solvents. In some embodiments, a substance is hydrophobic relative to another substance because it is more soluble in oil, non-polar solvents, or hydrophobic solvents than is the other substance. In some embodiments, a substance is hydrophobic relative to another substance because it is less soluble in water, polar solvents, or hydrophilic solvents than is the other substance.

In conjunction with: As used herein, the phrase "delivered in conjunction with" refers to the co-delivery of two or more substances or agents. In particular, according to the present invention, the phrase is used herein in reference to delivery of a biologically active agent with inventive nanoparticles and/or nanoparticle compositions. A substance or agent is delivered in conjunction with nanoparticles when the substance or agent is combined with nanoparticles and/or nanoparticle compositions; is encapsulated or completely surrounded by nanoparticles; is embedded within an nanoparticle micellar membrane; and/or is associated with the outer surface of an nanoparticle micellar membrane. A substance or agent to be delivered in conjunction with nanoparticles and/or nanoparticle compositions may or may not be covalently linked to the nanoparticles and/or nanoparticle compositions. A substance or agent to be delivered in conjunction with inventive nanoparticles and/or nanoparticle compositions may or may not be attached to the nanoparticles and/or nanoparticle compositions by adsorption forces.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than 90%, 91%, 92%, 93%, 94%, 95%, 96%, 97%, 98%, 99% pure.

Microfluidized: As used herein, the term "microfluidized" means exposed to high shear forces. In some embodiments, such exposure to high shear forces is accomplished by exposure to high pressure; in some embodiments such high pressure is within the range of about 15,000 to about 26,000 psi. In some embodiments, such exposure to high shear forces is accomplished by cavitation. In some embodiments, such exposure to high shear forces is accomplished by passing a sample through an instrument such as, for example, a Microfluidizer® (Microfluidics Corporation/MFIC Corporation) or other like device that may be useful in creating a uniform nanoparticle composition. In some embodiments of the present invention, a sample is microfluidized through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes. In some embodiments, the period of time is about 30 seconds. In some embodiments of the invention, a sample is "microfluidized" through a single exposure to high shear forces; such embodiments are referred to as "single pass" microfluidization.

Nanoparticle: As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane. A "micellar membrane" comprises amphiphilic entities which have aggregated to surround and enclose a space or compartment (e.g., to define a lumen).

Nanoparticle composition: As used herein, the term "nanoparticle composition" refers to any substance that contains at least one nanoparticle. In some embodiments, a nanoparticle composition is a uniform collection of nanoparticles. In some embodiments, nanoparticle compositions are dispersions or emulsions. In general, a dispersion or emulsion is formed when at least two immiscible materials are combined. An "oil-in-water" dispersion is one in which oily particles (or hydrophobic or non-polar) are dispersed within an aqueous dispersion medium. A "water-in-oil" dispersion is one in which aqueous (or hydrophilic or polar) particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. In some embodiments, nanoparticle compositions are nanoemulsions. In some embodiments, nanoparticle compositions comprise micelles. In some particular embodiments, a nanoparticle composition comprises amphiphilic entity nanoparticles as described in PCT application serial number PCT/US07/086018, entitled "AMPHIPHILIC ENTITY NANOPARTICLES," filed on Nov. 30, 2007 (incorporated herein by reference). In some embodiments, a nanoparticle composition is stable. In some embodiments, a nanoparticle composition includes one or more biologically active agents to be delivered in conjunction with the nanoparticles.

Nutraceutical: As used herein, the term "nutraceutical" refers to any substance thought to provide medical, health, or biological benefits. In some embodiments, nutraceuticals may prevent disease. In some embodiments, nutraceuticals may provide basic nutritional value. In some embodiments, a nutraceutical is a food or part of a food. In some embodiments, a nutraceutical agent may be a class of isolated nutrients, dietary supplements, vitamins, minerals, herbs, fortified foods, healing foods, genetically engineered foods, and processed foods. Nutraceuticals may also be known as "phytochemical foods" or "functional foods."

Premix: As used herein, the term "premix" refers to any combination of components that is subsequently used to generate a nanoparticle composition according to the present invention. For example, a premix is any collection of ingredients that, when subjected to high shear forces, generates nanoparticles according to the present invention. In some embodiments, a premix contains two or more immiscible solvents. In some embodiments, a premix contains components that self-assemble into nanoparticles. In some embodiments, a premix contains components that self-assemble into micelles. In some embodiments, a premix contains one or more amphiphilic entities as described in PCT application serial number PCT/US07/086018, entitled "AMPHIPHILIC ENTITY NANOPARTICLES," filed Nov. 30, 2007 (incorporated herein by reference). In some embodiments, a premix contains one or more unmodified peptides; in some embodiments, a premix contains at least one other biologically active agent. In some embodiments, a premix is agitated, mixed, and/or stirred; in some embodiments, a premix is agitated, mixed, and/or stirred prior to being subjected to high shear force. In some embodiments, a premix comprises at least one solubilized component (i.e., at least one component that is in solution); in some such embodiments, the premix is subjected to high shear force after such solubilization is achieved.

Pure: As used herein, a substance and/or entity is "pure" if it is substantially free of other components. For example, a preparation that contains more than about 90% of a particular substance and/or entity is typically considered to be a pure preparation. In some embodiments, a substance and/or entity is at least 91%, 92%, 93%, 94%, 95%, 96%, 97%, 98%, or 99% pure.

Shear force: As used herein, the term "shear force" refers to a force that is parallel to the face of a material, as opposed to a force that is perpendicular to the face of a material. In some embodiments, a composition exposed to high shear forces in order to produce a uniform nanoparticle composition. Any method known in the art can be used to generate high shear forces. In some embodiments, cavitation is used to generate high shear forces. In some embodiments, high pressure homogenization is used to generate high shear forces. Alternatively or additionally, high shear force may be administered by exposure to high pressure, for example about 15,000 psi. In some embodiments, such high pressure is within the range of about 18,000 to about 26,000 psi; in some embodiments, it is within the range of about 20,000 to about 25,000 psi. In some embodiments, a Microfluidizer® Processor (Microfluidics Corporation/MFIC Corporation) or other like device is used to generate high shear force. Microfluidizer® Processors provide high pressure and a resultant high shear rate by accelerating a composition through microchannels (typically having dimensions on the order of 75 microns) at a high velocity (typically in the range of 50 m/s-300 m/s) for size reduction to the nanoscale range. As the fluid exits the microchannels it forms jets which collide with jets from opposing microchannels. In the channels the fluid experiences high shear (up to $10^7$ 1/s) which is orders of magnitude higher than that of conventional technologies. Jet collisions result in mixing in submicron level. Therefore, in such devices, high shear and/or impact can achieve particle size reduction and mixing of multiphase. In some embodiments of the present invention, a sample is exposed to high shear forces for a period of time less than about 10 minutes. In some embodiments, the period of time is less than about 9, about 8, about 7, about 6, about 5, about 4, about 3, about 2, or about 1 minute(s). In some embodiments, the period of time is within the range of about 1 to about 2 minutes or less; in some embodiments, the period of time is about 30 seconds. In some embodiments of the invention, a sample is "microfluidized" through a single exposure to high shear forces; such embodiments are referred to herein as "single pass" microfluidization.

Small Molecule: In general, a "small molecule" is understood in the art to be an organic molecule that is less than about 5 kilodaltons (Kd) in size. In some embodiments, the small molecule is less than about 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Subject: As used herein, the term "subject" or "patient" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Stable: The term "stable," when applied to nanoparticle compositions herein, means that the compositions maintain one or more aspects of their physical structure (e.g., size range and/or distribution of particles) over a period of time. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, or longer. In some embodiments, the period of time is within the range of about one (1) day to about twenty-four (24) months, about two (2) weeks to about twelve (12) months, about two (2) months to about five (5) months, etc. For example, if a nanoparticle composition is subjected to prolonged storage, temperature changes, and/or pH changes and a majority of the nanoparticles in the population maintain a diameter within a stated range (i.e., for example, between approximately 10 nm-120 nm), the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9%, or more. In some embodiments of the invention, where a nanoparticle composition comprises one or more biologically active agents (e.g. unmodified peptide), the nanoparticle composition is considered stable if the concentration of biologically active agent is maintained in the composition over the designated period of time under a designated set of conditions.

Substantially free of: An inventive nanoparticle composition is said to be "substantially free of" particles whose diameter is outside of a stated range when no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Suffering from: An individual who is "suffering from" a disease, disorder, or condition (e.g., facial wrinkles) has been diagnosed with or exhibits symptoms of the disease, disorder, or condition.

Therapeutically effective amount: As used herein, the term "therapeutically effective amount" means an amount of inventive nanoparticle composition that is sufficient, when administered to a patient suffering from or susceptible to a disease, disorder, and/or condition, to treat the disease, disorder, and/or condition.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relives, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Toxic solvent: As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl foramide, chloroform, tetramethyl foramide, acetone, acetates, and alkanes.

Uniform: The term "uniform," when used herein in reference to a nanoparticle composition, refers to a nanoparticle composition in which the individual nanoparticles have a specified range of particle diameter sizes. For example, in some embodiments, a uniform nanoparticle composition is one in which the difference between the minimum diameter and maximum diameter does not exceed approximately 600, approximately 550, approximately 500, approximately 450, approximately 400, approximately 350, approximately 300, approximately 250, approximately 200, approximately 150, approximately 100, approximately 90, approximately 80, approximately 70, approximately 60, approximately 50, or fewer nm. In some embodiments, particles (e.g., unmodified-peptide-containing particles) within inventive uniform nanoparticle compositions have diameters that are smaller than about 600, about 550, about 500, about 450, about 400, about 350, about 300, about 250, about 200, about 150, about 130, about 120, about 115, about 110, about 100, about 90, about 80 nm, or less. In some embodiments, particles (e.g., unmodified-peptide-containing particles) within inventive uniform nanoparticle compositions have diameters within the range of about 10 and about 600 nanometers. In some embodiments, particles (e.g., unmodified-peptide-containing particles) within inventive uniform nanoparticle compositions have diameters within the range of about 10 to about 300, about 10 to about 200, about 10 to about 150, about 10 to about 130, about 10 to about 120, about 10 to about 115, about 10 to about 110, about 10 to about 100, or about 10 to about 90 nm. In some embodiments, particles (e.g., unmodified-peptide-containing particles) within inventive botulinum nanoparticle compositions have an average particle size that is under about 300, about 250, about 200, about 150, about 130, about 120, about 115, about 110, about 100, or about 90 nm. In some embodiments, the average particle size is within the range of about about 10 to about 300, about 50 to about 250, about 60 to about 200, about 65 to about 150, about 70 to about 130 nm. In some embodiments, the average particle size is about 80 to about 110 nm. In some embodiments, the average particle size is about 90 to about 100 nm. In some embodiments, a majority of the particles (e.g., unmodified-peptide-containing particles) within inventive uniform nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition. In some embodiments of the invention, a uniform nanoparticle composition is achieved by microfluidization of a sample. In some embodiments of the invention, a uniform nanoparticle composition is prepared by exposure to high shear force, e.g., by microfluidization.

Unmodified peptide: As used herein, the term "unmodified peptide" refers to a peptide that has not been chemically modified through the addition of other covalently-bonded functional groups intended to achieve transdermal delivery of the peptide. In some embodiments, the peptide has not been chemically modified to add pendant acetyl and/or palmitoyl groups. In some embodiments, the peptide has not been chemically modified to add any functional pendant groups.

DESCRIPTION OF CERTAIN EMBODIMENTS

Nanoparticles

As discussed herein, the present invention provides nanoparticle compositions that include one or more unmodified peptides. In some embodiments, such nanoparticle compositions further include one or more other biologically active agents in addition to the unmodified peptides. In some embodiments, the nanoparticle compositions are formulated with one or more other components, for example in a pharmaceutical or cosmetic preparation. In some embodiments, such a pharmaceutical or cosmetic preparation is formulated to achieve transdermal delivery of the unmodified peptides (and/or one or more other biologically active agents).

In some embodiments, inventive nanoparticle compositions are stable. In some embodiments, the nanoparticle compositions are uniform.

In some embodiments, a uniform nanoparticle composition comprises a population of particles whose difference between the minimum and maximum diameters does not exceed approximately 600 nm, approximately 550 nm, approximately 500 nm, approximately 450 nm, approximately 400 nm, approximately 350 nm, approximately 300 nm, approximately 250 nm, approximately 200 nm, approximately 150 nm, or approximately 100 nm.

In some embodiments, inventive nanoparticles have diameters that are smaller than about 1000, about 600, about 550, about 500, about 450, about 400, about 350, about 300, about 250, about 200, about 150, about 130, about 120, about 115, about 110, about 100, about 90, about 80, about 50 nm, or less.

In some embodiments, inventive nanoparticles have a diameter of 1 nm to 1000 nm, 1 nm to 600 nm, 1 nm to 500 nm, 1 nm to 400 nm, 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, inventive nanoparticles have a diameter of 1 nm to 15 nm, 15 nm to 200 nm, 25 nm to 200 nm, 50 nm to 200 nm, or 75 nm to 200 nm.

In some embodiments, the total particle distribution is encompassed within the specified range of particle diameter size. In some embodiments, less than 50%, 25%, 10%, 5%, or 1% of the total particle distribution is outside of the specified range of particle diameter sizes. In some embodiments, less than 1% of the total particle distribution is outside of the specified range of particle diameter sizes. In certain embodiments, the nanoparticle composition is substantially free of particles having a diameter larger than 300 nm, 250 nm, 200 nm, 150 nm, 120 nm, 100 nm, 75 nm, 50 nm, or 25 nm.

In some embodiments, nanoparticles within inventive nanoparticle compositions have an average particle size that is under about 300 nm, about 250 nm, about 200 nm, about 150 nm, about 130 nm, about 120 nm, about 115 nm, about 110 nm, about 100 nm, about 90 nm, or about 50 nm. In some embodiments, the average particle size is within the range of about 10 nm to about 300 nm, 50 nm to about 250 nm, 60 nm to about 200 nm, 65 nm to about 150 nm, or 70 nm to about 130 nm. In some embodiments, the average particle size is about 80 nm to about 110 nm. In some embodiments, the average particle size is about 90 to about 100 nm.

In some embodiments, inventive nanoparticle compositions are substantially free of particles having a diameter in excess of 300 nm. Specifically, in some embodiments, fewer than 50%, of the nanoparticles in inventive nanoparticle compositions have a diameter in excess of 300 nm. In some embodiments, fewer than 25% of the particles have a diameter in excess of 300 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 300 nm. Furthermore, in some embodiments, the nanoparticles in inventive nanoparticle compositions have diameters within the range of 10 nm to 300 nm.

In some embodiments, inventive nanoparticle compositions are substantially free of particles having a diameter in excess of 200 nm. Specifically, in some embodiments, fewer than 50%, of the nanoparticles in inventive nanoparticle compositions have a diameter in excess of 200 nm. In some embodiments, fewer than 25% of the particles have a diameter in excess of 200 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 200 nm. Furthermore, in some embodiments, the nanoparticles in inventive nanoparticle compositions have diameters within the range of 10 nm to 200 nm.

In some embodiments, inventive nanoparticle compositions are substantially free of particles having a diameter in excess of 120 nm. Specifically, in some embodiments, fewer than 50%, of the nanoparticles in inventive nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm. Furthermore, in some embodiments, the nanoparticles in inventive nanoparticle compositions have diameters within the range of 10 nm to 120 nm.

In some embodiments, a majority of the nanoparticles within inventive compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

Zeta potential is a measurement of the electric potential at a shear plane. A shear plane is an imaginary surface separating a thin layer of liquid bound to a solid surface (e.g. the surface of inventive nanoparticles) and showing elastic behavior from the rest of liquid (e.g. liquid dispersion medium) showing normal viscous behavior. In some embodiments, inventive nanoparticles have a zeta potential ranging between −50 mV to +50 mV. In some embodiments, inventive nanoparticles have a zeta potential ranging between −25 mV to +25 mV. In some embodiments, inventive nanoparticles have a zeta potential ranging between −10 mV to +10 mV.

In some embodiments inventive nanoparticle compositions are emulsions or dispersions. In general, an emulsion or dispersion is formed from at least two immiscible materials, one of which will constitute the dispersion medium (i.e., the liquid medium in which particles (e.g., nanoparticles, which constituted the "dispersed medium") are dispersed. An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. For example, emulsions or dispersions can be prepared from immiscible sets of hydrophobic/hydrophilic materials; polar/nonpolar materials, etc., regardless of whether such materials are strictly speaking "aqueous" or "oily."

In some embodiments, inventive nanoparticle compositions comprise micellar structures (e.g., the nanoparticles are micelles). In some embodiments, such micellar structures are crosslinked. In some embodiments, such micellar structures are not crosslinked.

In some embodiments, inventive nanoparticle compositions self-assemble from a collection of combined components. In some embodiments, inventive nanoparticle compositions are prepared by subjecting a combination of components (i.e., a "premix") to high shear force. In some embodiments, high shear force is applied by high pressure, by cavitation, by homogenization, and/or by microfluidization. In some embodiments, combined nanoparticle-forming components are agitated, stirred, or otherwise mixed. In some such embodiments, the components are subjected to high shear force after having been mixed. In some specific embodiments, mixing may be performed for a period of time such as, for example, less than one hour or more than 5, 6, 7, 8, 9, 10, 11, 12, 13, 14, or 15 hours. In some embodiments, solubilization is achieved.

In some embodiments of the invention, production of nanoparticle compositions involves dialyzing a collection of components, for example to remove any organic solvent, and/or freeze-drying to produce a composition.

In some embodiments of the present invention that utilize a premix, it is to be understood that the premix components may assemble into particles before the application of high shear force. At least some of such particles may be microparticles or even nanoparticles. In some embodiments, an inventive nanoparticle composition is prepared from a premix, wherein the premix is selected from the group comprising a suspension or a microemulsion. In some embodiments, however, particle structures do not form in the premix before application of high shear force.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear stress.

In certain embodiments of the invention, the premix is prepared as a solution prior to application of high shear force. In particular, for nanoparticle compositions that include at least one biologically active agent (e.g., an unmodified peptide), it is often desirable for the biologically active agent to be dissolved in the premix before the high shear stress is applied. Thus, in many embodiments, the biologically active agent is soluble in at least one of the media (or in a combination of media utilized in the premix). In some embodiments of the invention, such dissolution requires heating; in other embodiments it does not.

In some embodiments of the invention, nanoparticle compositions are prepared from components including one or more aqueous, polar, or hydrophilic medium(a), one or more oily, nonpolar, or hydrophobic medium(a), one or more micelle components, one or more surfactants or emulsifiers, one or more biologically active agents and/or one or more release retarding agents, etc.

Those of ordinary skill in the art will be well aware of suitable aqueous media that can be used as dispersion media or as media to be dispersed in accordance with the present invention. Representative such aqueous media include, for example, water, saline solutions (including phosphate buffered saline), water for injection, short chain alcohols, 5% dextrose, Ringer's solutions (lactated Ringer's injection, lactated Ringer's plus 5% dextrose injection, acylated Ringer's injection), Normosol-M, Isolyte E, and the like, and combinations thereof.

Those of ordinary skill in the art will also be well aware of suitable oily media that can be used as dispersion media or as media to be dispersed in accordance with the present invention. In some embodiments, the oil may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride. In certain embodiments, the oil is a medium chain (e.g., 6-12 carbons) triglyceride (e.g., Labrafac WL 1349, coconut oil, palm kernel oil, camphor tree drupe oil, etc.). In certain embodiments, the oil is a short chain (e.g., 2-5 carbons) triglyceride. In certain embodiments, the oil is a long chain (e.g., greater than 12 carbons) triglyceride (e.g., soybean oil, sunflower oil, etc.).

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mineral, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, wheat germ, and mixtures thereof. Suitable synthetic oils for use with the present invention include, but are not limited to: caprylic/capric triglyceride, cyclomethicone, diethyl sebacate, dimethicone 360, isopropyl myristate, octyldodecanol, oleyl alcohol, and combinations thereof.

Appropriate micelle components may include, for example, one or more amphiphilic entities. Useful amphiphilic entities include natural entities, synthetic entities, and entities that contain both natural and synthetic components. In some embodiments, amphiphilic entities may comprise one or more polymers, and/or one or more compounds with polymeric character.

In general, an amphiphilic entity is one that has both hydrophobic and hydrophilic natures. As will be appreciated by those of ordinary skill in the art, an amphiphilic entity can be comprised in any number of different ways. In some embodiments, an amphiphilic entity may comprise one or more individual compounds or molecules that is itself amphiphilic. To give but a few examples, such compounds or molecules include polyethylene glycol (PEG), phospholipids, cholesterols, glycolipids fatty acids, bile acids, and saponins PEG is generally recognized as safe for use in food, cosmetics, and medicines by the US Food and Drug Administration. PEG is water-soluble, non-toxic, odorless, lubricating, nonvolatile, and nonirritating.

In some embodiments, an amphiphilic entity may comprise one or more individual components that is not itself amphiphilic but that has some hydrophilic or hydrophobic character. In such embodiments, two or more such non-amphiphilic components will typically be associated with one another such that the assemblage of the individual components is amphiphilic. Such association may or may not involve covalent linkage; such association may involve non-covalent bonding (e.g., via electrostatic interactions, affinity interactions, hydrophobic interactions, hydrogen bonding, Van der Waals interactions, ionic interaction, dipole-dipole interaction, etc.). In general, such association may involve any relevant force, bond, or means of adhesion.

In some embodiments, an amphiphilic entity for use in accordance with the present invention may be constructed from two or more individual components having differing degrees of hydrophilicity or hydrophobicity. In certain embodiments, an amphiphilic entity may comprise at least one hydrophilic component and at least one hydrophobic component. In certain embodiments, the "hydrophilic" and "hydrophobic" components are either hydrophilic or hydrophobic relative to one another.

In some embodiments, two or more components of differing degrees of hydrophilicity or hydrophobicity may be bonded together by covalent bonds to form a homopolymer or a co-polymer. In some embodiments, a co-polymer may be a block co-polymer. In some embodiments, a co-polymer may be a graft co-polymer.

In some embodiments, an amphiphilic entity may comprise or consist of an amphiphilic block co-polymer. In some embodiments, an amphiphilic block co-polymer may be a diblock co-polymer. In certain embodiments, an amphiphilic diblock co-polymer may comprise a first polymer block and a second polymer block connected covalently at the chain ends. In specific embodiments, the first polymer block may comprise repeating units of a hydrophilic component, and the second polymer block may comprise repeating units of a hydrophobic component. In specific embodiments, the first polymer block may comprise repeating units of a hydrophobic component, and the second polymer block may comprise repeating units of a hydrophilic component. In some embodiments, an amphiphilic block co-polymer may be a multiblock co-polymer. In certain embodiments, an amphiphilic block co-polymer may comprise multiple alternating blocks of two or more polymers connected covalently at the chain ends. In specific embodiments, an amphiphilic block co-polymer may comprise multiple alternating hydrophilic blocks and hydrophobic blocks connected covalently at the chain ends. In specific embodiments, each block of the alternating blocks may comprise repeating units of either hydrophilic components or hydrophobic components.

In some embodiments, an amphiphilic entity may comprise or consist of an amphiphilic graft co-polymer. In some embodiments, an amphiphilic graft co-polymer may comprise or consist of blocks of polymers connected covalently to the side chains of other blocks of polymers. In specific embodiments, each polymer block may comprise or consist of repeating units of either hydrophilic or hydrophobic components. In certain embodiments, an amphiphilic graft co-polymer may comprise or consist of a first polymer block and a second polymer block connected covalently to a side chain of the first polymer block. In certain embodiments, the first polymer block may comprise or consist of repeating units of a hydrophilic component, and the second block may comprise repeating units of a hydrophobic component. In certain embodiments, the first polymer block may comprise or consist of repeating units of a hydrophobic component, and the second block may comprise repeating units of a hydrophilic component.

In some embodiments, an amphiphilic block or graft co-polymer may include a hydrophilic polymer block comprising repeating units of a polysaccharide and a hydrophobic polymer block comprising repeating units of a polyester or polysaccharide. Alternatively or additionally, an amphiphilic block or graft co-polymer may include a hydrophobic polymer block comprising repeating units of a polysaccharide and a hydrophilic polymer block comprising repeating units of a polyester or polysaccharide. Such a hydrophilic polymer block can contain repeating units of any type of hydrophilic polymer, such as a polysaccharide (e.g. pullulan) or polyalkene oxide (e.g. polyethylene oxide). The hydrophobic polymer block can contain repeating units of any type of hydrophobic polymer, such as a polycaprolactone or polyamide (e.g. polycaprolactam).

In some embodiments, the hydrophobic portion of the amphiphilic entity may be non-ionic. In some embodiments, the hydrophilic component of an amphiphilic entity comprises one or more ionic groups. In general, such ionic groups are hydrophilic and can confer hydrophilic nature on the amphiphilic entity.

In some embodiments, the ionic group may be cationic. In some embodiments, the cationic group may be an ammonium ($NH_4^+$), nitronium ($NO_2^+$), nitrosyl ($NO^+$), hydronium ($H_3O^+$), mercurous ($Hg_2^{2+}$), phosphonium ($PH_4^+$), vanadyl ($VO^{2+}$), or salt thereof.

In some embodiments, the ionic group may be anionic. In some embodiments, the anionic group may be a fatty acid, arsenide ($As^{3-}$), azide ($N_3^-$), bromide ($Br^-$), chloride ($Cl^-$), fluoride ($F^-$), hydride ($H^-$), iodide ($I^-$), nitride ($N^{3-}$), oxide ($O^{2-}$), phosphide ($P^{3-}$), selenide ($Se^{2-}$), sulfide ($S^{2-}$), peroxide ($O_2^{2-}$), arsenate ($AsO_4^{3-}$), arsenite ($AsO_3^{3-}$), borate ($BO_3^{3-}$), perbromate ($BrO_4^-$), bromate ($BrO_3^-$), bromite ($BrO_2^-$), hypobromite ($BrO^-$), carbonate ($CO_3^{2-}$), hydrogen carbonate ($HCO_3^-$), chlorate ($ClO_3^-$), perchlorate ($ClO_4^-$), chlorite ($ClO_2^-$), hypochlorite ($ClO^-$), chromate ($CrO_4^{2-}$), dichromate ($Cr_2O_7^{2-}$), perfluorate ($BrO_4^-$), fluorate ($BrO_3^-$), fluorite ($BrO_2^-$), hypofluorite ($BrO^-$), periodate ($IO_4^-$), iodate ($IO_3^-$), iodite ($IO_2^-$), hypoiodite ($IO^-$), nitrate ($NO_3^-$), nitrite ($NO_2^-$), phosphate ($PO_4^{3-}$), hydrogen phosphate ($HPO_4^{2-}$), dihydrogen phosphate ($H_2PO_4^-$), phosphite ($PO_3^{3-}$), silicate ($SiO_3^{2-}$), sulfate ($SO_4^{2-}$), thiosulfate ($S_2O_3^{2-}$), hydrogen sulfate ($HSO_4^-$), sulfite ($SO_3^{2-}$), hydrogen sulfite ($HSO_3^-$), sulfonate ($-S(=O)_2-O^-$), acetate ($C_2H_3O_2^-$), formate ($HCO_2^-$), oxalate ($C_2O_4^{2-}$), hydrogen oxalate ($HC_2O_4^-$), citrate ($C_6H_5O_7^{3-}$), succinate ($C_4H_4O_4^{2-}$), fumarate ($C_4H_2O_4^{2-}$), malate ($C_4H_5O_5^{2-}$), hydrogen sulfide ($HS^-$), telluride ($Te^{2-}$), amide ($NH_2^-$), cyanate ($OCN^-$), thiocyanate ($SCN^-$), cyanide ($CN^-$), hydroxide ($OH^-$), permanganate ($MnO_4^-$), or salt thereof.

In some embodiments, the hydrophilic component of an amphiphilic entity may comprise or consist of a nucleic acid. For example, the nucleic acid polymer may include DNA, RNA, or combinations thereof. In some embodiments, the nucleic acid polymer may be an oligonucleotide and/or polynucleotide. In some embodiments, the nucleic acid polymer may be an oligonucleotide and/or modified oligonucleotide; an antisense oligonucleotide and/or modified antisense oligonucleotide; a cDNA; a genomic DNA; viral DNA and/or RNA; DNA and/or RNA chimeras; plasmids; cosmids; gene fragments; an artificial and/or natural chromosome (e.g. a yeast artificial chromosome) and/or a part thereof; an RNA (e.g. an mRNA, a tRNA, an rRNA and/or a ribozyme); a peptide nucleic acid (PNA); a polynucleotide comprising synthetic analogues of nucleic acids, which may be modified or unmodified; various structural forms of DNA including single-stranded DNA, double-stranded DNA, supercoiled DNA and/or triple-helical DNA; Z-DNA; and/or combinations thereof.

In some embodiments, the hydrophilic component of an amphiphilic entity may comprise or consist of a carbohydrate. In some embodiments, the carbohydrate may be a polysaccharide composed of simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, the polymer may be a hydrophilic carbohydrate, including aminated, carboxylated, and sulfated polysaccharides. In some embodiments, the hydrophilic carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

In some embodiments, the hydrophilic component of an amphiphilic entity may comprise or consist of a gum including, but not limited to, xanthan gum, alginic acid, caraya gum, sodium alginate, and/or locust bean gum.

In some embodiments, a component of an amphiphilic entity may comprise or consist of a protein. In some embodiments, a protein is a hydrophilic component of an amphiphilic entity. In other embodiments, a protein is a hydrophobic component of an amphiphilic entity. Exemplary proteins that may be used in accordance with the present invention include, but are not limited to, albumin, collagen, or a poly(amino acid) (e.g. polylysine).

In some embodiments, the hydrophobic component of an amphiphilic entity may comprise or consist of one or more fatty acid groups or salts thereof. In general, such groups are typically hydrophobic and can confer hydrophobic nature onto the amphiphilic entity. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, the hydrophobic component of an amphiphilic entity may comprise or consist of one or more biocompatible and/or biodegradable synthetic polymers, including, for example, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumarates, polycaprolactones, polyamides (e.g. polycaprolactam), polyacetals, polyethers, polyesters (e.g. polylactide and polyglycolide), biodegradable polycyanoacrylates, polyvinyl alcohols, and biodegradable polyurethanes. For example, the amphiphilic entity may comprise one or more of the following biodegradable polymers: poly(lactic acid), poly(glycolic acid), poly(caprolactone), poly(lactide-co-glycolide), poly(lactide-co-caprolactone), poly(glycolide-co-caprolactone), and poly(DL-lactide-co-glycolide).

In some embodiments, the hydrophobic component of an amphiphilic entity may comprise or consist of one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully-polymerized copolymers of acrylic and methacrylic acid esters with a low content of quaternary ammonium groups.

In some embodiments, the hydrophobic component of an amphiphilic entity may comprise or consist of a polyester. Exemplary such polyesters include, for example, polyalkylene glycols, poly(glycolide-co-lactide), PEGylated poly(lactic-co-glycolic acid), poly(lactic acid), PEGylated poly(lactic acid), poly(glycolic acid), PEGylated poly(glycolic acid), co-polymers of polylactic and polyglycolic acid, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), and derivatives thereof. In some embodiments, polyesters may include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

Suitable surfactants or emulsifying agents include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; tyloxapol; poly(ethylene glycol)5000-phosphatidylethanolamine; poly(ethylene glycol)400-monostearate; and phospholipids. The surfactant component may be a mixture of different surfactants. These surfactants may be extracted and purified from a natural source or may be prepared synthetically in a laboratory. In a preferred embodiment, the surfactants are commercially available.

In certain embodiments of the invention, relative amounts of components utilized to prepare inventive nanoparticle compositions are selected or adjusted to generate nanoparticles having desired characteristics. In some embodiments, the oil and surfactant are utilized at a ratio ranging between 0.25-10. In some embodiments, the ratio of oil to surfactant is approximately 0.25:1, approximately 0.5:1, approximately 1:1, approximately 2:1, approximately 3:1, approximately 4:1, approximately 5:1, approximately 6:1, approximately 7:1, approximately 8:1, approximately 9:1, or approximately 10:1. In some embodiments, the ratio of surfactant to oil is approximately 0.5:1, approximately 1:1, approximately 2:1, approximately 3:1, approximately 4:1, approximately 5:1, approximately 6:1, approximately 7:1, approximately 8:1, approximately 9:1, or approximately 10:1. In some embodiments, the oil and surfactant are utilized at a ratio ranging between 0.25-2. In some embodiments, the ratio of oil to surfactant is approximately 0.25:1, approximately 0.5:1, approximately 1:1, or approximately 2:1. In some embodiments, the ratio of surfactant to oil is approximately 0.5:1, approximately 1:1, or approximately 2:1. In certain embodiments, the ratio of oil to surfactant is approximately 1:1.

In some embodiments, the percent of oil in the composition from which nanoparticles are prepared (e.g., in the premix) ranges between 0% to 30%. In some embodiments the percent of oil in the composition from which nanoparticles are prepared (e.g., in the premix) is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29%, or approximately 30%. In some embodiments the percent of oil is approximately 8%. In some embodiments the percent of oil is approximately 5%.

In some embodiments, where one or more amphiphilic entities is/are utilized, the percent of amphiphilic entity in the composition from which nanoparticles are prepared (e.g., in the premix) can range from 40% to 99%, from 50% to 99%, from 60% to 99%, from 70% to 99%, from 80% to 99%, from 80% to 90%, or from 90% to 99%. In some embodiments the percent of amphiphilic entity in the composition from which nanoparticles are prepared (e.g., in the premix) is approximately 75%, approximately 76%, approximately 77%, approximately 78%, approximately 79%, approximately 80%, approximately 81%, approximately 82%, approximately 83%, approximately 84%, approximately 85%, approximately 86%, approximately 87%, approximately 88%, approximately 89%, approximately 90%, approximately 91%, approximately 92%, approximately 93%, approximately 94%, approximately 95%, approximately 96%, approximately 97%, approximately 98%, or approximately 99%.

The percent of substances with surfactant activity in the premix can range from 0% to 99%, from 10% to 99%, from 25% to 99%, from 50% to 99%, or from 75% to 99%. In some embodiments, the percent of substances with surfactant activity in the premix can range from 0% to 75%, from 0% to 50%, from 0% to 25%, or from 0% to 10%. In some embodiments, the percent of surfactant in the composition from which nanoparticles are prepared (e.g., in the premix) ranges between 0%-30%. In some embodiments the percent of surfactant in is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29%, or approximately 30%. In some embodiments the percent of surfactant is approximately 8%. In some embodiments the percent of surfactant is approximately 5%.

In some embodiments, the nanoparticle composition does not contain more than one oil. In some embodiments, the nanoparticle composition may comprise two or more oils. In some embodiments, the nanoparticle composition does not contain more than one surfactant. In some embodiments, the nanoparticle composition may comprise two or more surfactants. In some embodiments, the nanoparticle composition is completely free or substantially free of toxic components.

In some embodiments, the nanoparticle composition consists essentially of water, an oil, a surfactant, and at least one biologically active agent (e.g., and unmodified peptide). In some embodiments, the nanoparticle composition consists essentially of water, an oil, a surfactant, at least one biologically active agent, and at least one substance used to produce and/or preserve the nanoparticle composition.

In some embodiments, the nanoparticle composition consists of water, an oil, a surfactant, and an unmodified peptide. In some embodiments, the nanoparticle composition consists of water, an oil, a surfactant, an unmodified peptide, and at least one substance used to produce and/or preserve the nanoparticle.

Unmodified Peptides

Any of a variety of peptides may be incorporated in nanoparticle compositions according to the present invention. In most embodiments, it a peptide is less than about 100 amino acids in length; in some embodiments, a peptide is less than about 90, about 80, about 70, about 65, about 60, about 55, about 50, about 45, about 40, about 35, about 30, about 25, about 20, about 15, about 13, about 12, about 10, about 9, about 8, about 7, about 6, or about 5 amino acids in length. In some specific embodiments, the peptide is a penta peptide. In some embodiments, a peptide to be incorporated in a nanoparticle compositions is comprised solely of naturally occurring amino acids. In some embodiments, a peptide comprises one or more non-naturally occurring amino acid.

Unmodified short peptides for use in accordance with the present invention, generally, are ones that have biological activity in the skin (including epidermis and dermis), subcutaneous tissue (including adipose tissue) and/or contiguous muscles. Such peptides include, but are not limited to, peptides to promote extra-cellular matrix production (e.g., KTTKS, SEQ ID NO.: 1; EYKTTKSSRL, SEQ ID NO.: 2; VIEYKTTK, SEQ ID NO.: 3; KTTK, SEQ ID NO.: 4; GKTVIEYKTTKS, SEQ ID NO.: 5; GKTVIEYK-TTKSSRL, SEQ ID NO.: 6; WGKTVIEYKTTKSSRLPIID, SEQ ID NO.: 7; CTSHTGAWGKTVIEYKTTKS, SEQ ID NO.: 8; TTKS, SEQ ID NO.: 9), peptides that may decrease wrinkles (e.g., EEMQRR, SEQ ID NO.: 10), peptides to improve wound healing (e.g., gastrin-releasing peptide, VGVAPG, SEQ ID NO.: 11; YYRADA, SEQ ID NO.: 12; GHK, SEQ ID NO.: 13, interferon, interferon inducer), and peptides (e.g., P144; TSLDASIIWAMMQN, SEQ ID NO.: 14) to treat excessive accumulation of extra-cellular matrix that are result in conditions such as hypertrophic scarring, keloids, and localized or systemic sclerosis (scleroderma) (Katayama, et al.; supra, Lupo, supra; Robinson et al., supra; Bhartiya et al., 1992, *J. Cell. Physiol.*, 150:312; and Santiago et al., 2005, *J. Investigative Dermatology*, 125:450; all of which are incorporated herein by reference). See Table 1 below for definitions of peptide abbreviations. and/or dermatological agents, may be delivered according to the present invention. Such biologically active agents may

TABLE 1

Peptide Abbreviations

| Trivial name[a] | Symbols[b] | | Systematic Name[c] | Formula |
|---|---|---|---|---|
| Alanine | Ala | A | 2-Aminopropanoic acid | $CH_3—CH(NH_2)—COOH$ |
| Arginine | Arg | R | 2-Amino-5-guanidinopentanoic acid | $H_2N—C(=NH)—NH—[CH_2]_3—CH(NH_2)—COOH$ |
| Asparagine | Asn[d] | N[d] | 2-Amino-3-carbamoylpropanoic acid | $H_2N—CO—CH_2—CH(NH_2)—COOH$ |
| Aspartic acid | Asp[d] | D[d] | 2-Aminobutanedioic acid | $HOOC—CH_2—CH(NH_2)—COOH$ |
| Cysteine | Cys | C | 2-Amino-3-mercaptopropanoic acid | $HS—CH_2—CH(NH_2)—COOH$ |
| Glutamine | Gln[d] | Q[d] | 2-Amino-4-carbamoylbutanoic acid | $H_2N—CO—[CH_2]_2—CH(NH_2)—COOH$ |
| Glutamic acid | Glu[d] | E[d] | 2-Aminopentanedioic acid | $HOOC—[CH_2]_2—CH(NH_2)—COOH$ |
| Glycine | Gly | G | Aminoethanoic acid | $CH_2(NH_2)—COOH$ |
| Histidine | His | H | 2-Amino-3-(1H-imidazol-4-yl)-propanoic acid | (imidazole structure) $CH_2—CH(NH_2)—COOH$ |
| Isoleucine | Ile | I | 2-Amino-3-methylpentanoic acid[e] | $C_2H_5—CH(CH_3)—CH(NH_2)—COOH$ |
| Leucine | Leu | L | 2-Amino-4-methylpentanoic acid | $(CH_3)_2CH—CH_2—CH(NH_2)—COOH$ |
| Lysine | Lys | K | 2,6-Diaminohexanoic acid | $H_2N—[CH_2]_4—CH(NH_2)—COOH$ |
| Methionine | Met | M | 2-Amino-4-(methylthio)butanoic acid | $CH_3—S—[CH_2]_2—CH(NH_2)—COOH$ |
| Phenylalanine | Phe | F | 2-Amino-3-phenylpropanoic acid | $C_6H_5—CH_2—CH(NH_2)—COOH$ |
| Proline | Pro | P | Pyrrolidine-2-carboxylic acid | (pyrrolidine-COOH structure) |
| Serine | Ser | S | 2-Amino-3-hydroxypropanoic acid | $HO—CH_2—CH(NH_2)—COOH$ |
| Threonine | Thr | T | 2-Amino-3-hydroxybutanoic acid[e] | $CH_3—CH(OH)—CH(NH_2)—COOH$ |
| Tryptophan | Trp | W | 2-Amino-3-(1H-indol-3-yl)-propanoic acid | (indole structure) $CH_2—CH(NH_2)—COOH$ |
| Tyrosine | Tyr | Y | 2-Amino-3-(4-hydroxyphenyl)-propanoic acid | $HO—$(phenyl)$—CH_2—CH(NH_2)—COOH$ |
| Valine | Val | V | 2-Amino-3-methylbutanoic acid | $(CH_3)_2CH—CH(NH_2)—COOH$ |

Other Components

As indicated herein, inventive nanoparticle compositions may contain or be combined with one or more other components. Certain exemplary such other components are discussed here.

Biologically-Active Agents

Any biologically active agents, including, for example, therapeutic, diagnostic, prophylactic, nutritional, cosmetic, and/or dermatological agents, may be delivered according to the present invention. Such biologically active agents may be small molecules, organometallic compounds, nucleic acids, proteins (including multimeric proteins, protein complexes, etc.), peptides, lipids, carbohydrates, herbs, hormones, metals, radioactive elements and compounds, drugs, vaccines, immunological agents, etc., and/or combinations thereof. Such biologically agents may be encapsulated within, adsorbed to the surface of, present at the interface of and/or present within a micellar membrane of inventive nanoparticles.

In some embodiments, the percent of biologically active agent in the composition used to prepare inventive nanoparticles (e.g., in the premix) and/or in the nanoparticles ranges from 0.1%-25%. In some embodiments, the percentage of biologically active agent ranges from 0.1%-20%, from 0.1%-15%, from 0.1%-10%, from 0.1%-5%, or from 0.1%-1%. In some embodiments, the percentage of biologically active agent ranges from 1%-20%, from 5%-20%, from 10%-20%, from 15%-20%, or from 15%-25%. In some embodiments, the percentage of biologically active agent is less than 0.1%. In some embodiments, the percentage of biologically active agent is greater than 25%. In some embodiments, the percentage of biologically active agent is approximately 0.1%, approximately 0.5%, approximately 1%, approximately 2%, approximately 3%, approximately 4%, approximately 5%, approximately 6%, approximately 7%, approximately 8%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, or greater.

Relevant biologically active agents can be produced or obtained according to any available method or approach. Biologically active agents may contain, or be modified to contain, one or more moieties intended to facilitate their use or delivery in conjunction with inventive nanoparticles. Such modification should not interfere with the biological activity of the agent. In some embodiments, the modification can optionally be removed in vivo. For example, biologically active agents may be detectably labeled and/or may be provided in a "pro" form that is converted or modified after delivery into an active form.

In some embodiments, the biologically active agent is a small molecule and/or organic compound with pharmaceutical activity. In some embodiments, the biologically active agent is a clinically-used drug. In some embodiments, the drug is an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, etc. Of particular interest are biologically active agents suitable for transdermal administration.

The biologically active agents delivered may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, the biologically active agent is a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, the biologically active agent is a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococccus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In some embodiments, the biologically active agent may be a protein. As used herein, the terms "protein" and "peptide" can be used interchangeably. In certain embodiments, peptides range from about 5 to about 40, about 10 to about 35, about 15 to about 30, or about 20 to about 25 amino acids in size. Peptides from panels of peptides comprising random sequences and/or sequences which have been varied consistently to provide a maximally diverse panel of peptides may be used.

In some embodiments, the biologically active agent may be an antibody. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library.

In some embodiments, the biologically active agent may be a nucleic acid. In some embodiments, the oligonucleotides comprise DNA, RNA, chimeric mixtures, derivatives, characteristic portions, and/or modified versions thereof. The oligonucleotides of the present invention may be single-stranded and/or double-stranded. The oligonucleotide may be modified at the base moiety, sugar moiety, and/or phosphate backbone, for example, to improve stability of the molecule, hybridization, etc.

In specific embodiments, a nucleic acid comprises an antisense molecule that binds to a translational start site, transcriptional start site, and/or splice junctions. Antisense oligonucleotides will bind to a target mRNA and/or prevent translation. Alternatively or additionally, the antisense oligonucleotide may bind to DNA of a target gene, such as, for example, a regulatory element.

In some embodiments, a nucleic acid comprises a ribozyme designed to catalytically cleave target mRNA transcripts may be used to prevent translation of a target mRNA and/or expression of a target (see, e.g., PCT publication WO 90/11364; and Sarver et al., 1990, *Science* 247:1222; both of which are incorporated herein by reference).

Alternatively or additionally, endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, *Anticancer Drug Des.* 6:569; Helene et al., 1992, *Ann, N.Y. Acad. Sci.* 660:27; and Maher, 1992, *Bioassays* 14:807; all of which are incorporated herein by reference).

In some embodiments, the biologically active agent is a nutraceutical agent. In some embodiments, the nutraceutical agent provides basic nutritional value. In some embodiments, the nutraceutical agent provides health or medical benefits. In some embodiments, the nutraceutical agent is a dietary supplement.

In some embodiments, the nutraceutical agent is a vitamin. In some embodiments, the vitamin is one or more of vitamin A (retinoids), vitamin B1 (thiamine), vitamin B2 (riboflavin), vitamin B3 (niacin), vitamin B5 (pantothenic acid), vitamin B6 (pyroxidone), vitamin B7 (biotin), vitamin B9 (folic acid), vitamin B12 (cyanobalamin), vitamin C (ascorbic acid), vitamin D, vitamin E, or vitamin K.

In some embodiments, the nutraceutical agent is a mineral. In some embodiments, the mineral is one or more of bismuth, boron, calcium, chlorine, chromium, cobalt, copper, fluorine, iodine, iron, magnesium, manganese, molybdenum, nickel, phosphorus, potassium, rubidium, selenium, silicon, sodium, strontium, sulfur, tellurium, titanium, tungsten, vanadium, or zinc.

In some embodiments, the nutraceutical agent is an essential amino acid. In some embodiments, the amino acid is one or more of arginine, glutamine, histidine, isoleucine, leucine, lysine, methionine, phenylalanine, threonine, tryptophan, or valine.

In some embodiments, nutraceutical agents may include fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics. In some embodiments, nutraceutical agents may include bio-engineered foods genetically-engineered to have a desired property (also known as "pharmafoods").

Exemplary nutraceutical agents and dietary supplements are disclosed, for example, in Roberts et al., (*Nutriceuticals: The Complete Encyclopedia of Supplements, Herbs, Vitamins, and Healing Foods*, American Nutriceutical Association, 2001; incorporated herein by reference). Nutraceutical agents and dietary supplements are also disclosed in *Physicians' Desk Reference for Nutritional Supplements*, 1st Ed., 2001, and *Physicians' Desk Reference for Herbal Medicines,* 1st Ed., 2001 (both of which are incorporated herein by reference).

In some embodiments, inventive nanoparticles loaded with nutraceutical agents can be incorporated into food substances. For example, the nutraceutical-loaded nanoparticles can be dissolved into liquids, such as beverages.

In some embodiments, the biologically active agent is a cosmetic and/or dermatological agent. In some embodiments, the cosmetic and/or dermatological agent may include vitamins and their derivatives (e.g. vitamin E and its esters, vitamin C and its esters, vitamins B, vitamin A alcohol or retinol and its esters), provitamins (e.g. panthenol, niacinamide or ergocalciferol), antioxidants, phenolic compounds (e.g. benzoyl peroxide), essential oils, humectants, sunscreen agents, moisturizing agents, proteins, ceramides, and pseudoceramides.

In some embodiments, the biologically active agent may be one or more botulinum toxin peptides or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

Those skilled in the art will recognize that this is an exemplary, not comprehensive, list of biologically active agents. Any biologically active agent may be encapsulated within or bound to the surface of nanoparticles.

Release Retarding Agents

In some embodiments of the invention, particularly those containing one or more biologically active agents (e.g., unmodified peptides), inventive nanoparticle compositions further include or are formulated with one or more release-retarding ingredients to allow for controlled release of the agent. Any release-retarding ingredient known in the art is suitable for use in making the inventive nanoparticles. In some embodiments, release-retarding ingredients are hydrophilic and/or hydrophobic polymers. Release-retarding ingredients include, for example celluloses or derivatives thereof, acrylic polymers, ester polymers, vinyl-pyrrolidone-based polymers, gums, other natural polymers, and/or combinations of these.

In some embodiments, the release-retarding ingredient is cellulose or a derivative thereof. In certain embodiments, the cellulose or derivative thereof comprises one or more of hydroxypropyl methylcellulose, methylcellulose, carboxymethylcellulose, sodium carboxymethylcellulose, hydroxypropyl ethylcellulose, hydroxyethylcellulose, and hydroxypropyl cellulose. In certain embodiments, the cellulose or derivative thereof is methylcellulose or a derivative thereof. In certain embodiments, the cellulose or derivative thereof is hydroxypropyl methylcellulose (HPMC). Those skilled in the art will appreciate that other cellulosic polymers, including other alkyl cellulosic polymers, can be utilized.

In some embodiments, the release-retarding ingredient is an acrylic polymer. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully polymerized copolymers of acrylic and methacrylic acid esters with a low content of quaternary ammonium groups.

In some embodiments, the release-retarding ingredient is a polyester. In some embodiments, polyesters include polyalkylene glycols, poly(glycolide-co-lactide), PEGylated poly(lactic-co-glycolic acid), poly(lactic acid), PEGylated poly(lactic acid), poly(glycolic acid), PEGylated poly(glycolic acid), co-polymers of polylactic and polyglycolic acid, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly (ethylene imine), PEGylated poly(ethylene imine), and derivatives thereof. In some embodiments, polyesters include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

In some embodiments, the release-retarding ingredient is a cross-linked polymer of poly(vinyl-pyrrolidone). In some embodiments, the polymer is crosspovidone. In some embodiments, the polymer is un-cross-linked poly(vinyl-pyrrolidone). In some embodiments, the polymer is povidone.

In some embodiments, the release-retarding ingredient may be a natural polymer. In some embodiments, the natural polymer is a gum, including, for example, xanthan gum, alginic acid, caraya gum, sodium alginate, and/or locust bean gum. In some embodiments, the natural polymer may be a protein (e.g. albumin), lipid, nucleic acid, or carbohydrateiments, the release-retarding ingredient is a polyester. In some embodiments, polyesters include polyalkylene glycols, poly(glycolide-co-lactide), PEGylated poly(lactic-co-glycolic acid), poly(lactic acid), PEGylated poly(lactic acid), poly(glycolic acid), PEGylated poly(glycolic acid), co-polymers of polylactic and polyglycolic acid, and derivatives thereof. In some embodiments, polyesters include, for example, polyanhydrides, poly(ortho ester) PEGylated poly (ortho ester), poly(caprolactone), PEGylated poly(caprolactone), polylysine, PEGylated polylysine, poly(ethylene imine), PEGylated poly(ethylene imine), and derivatives thereof. In some embodiments, polyesters include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

In some embodiments, the release-retarding ingredient is a cross-linked polymer of poly(vinyl-pyrrolidone). In some embodiments, the polymer is crosspovidone. In some embodiments, the polymer is un-cross-linked poly(vinyl-pyrrolidone). In some embodiments, the polymer is povidone.

In some embodiments, the release-retarding ingredient may be a natural polymer. In some embodiments, the natural polymer is a gum, including, for example, xanthan gum, alginic acid, caraya gum, sodium alginate, and/or locust bean gum. In some embodiments, the natural polymer may be a protein (e.g. albumin), lipid, nucleic acid, or carbohydrate Formulating Agents Inventive nanoparticle compositions may be formulated for administration to a subject. In certain embodiments, inventive nanoparticle compositions are formulated for application to the skin, to achieve transdermal delivery to the subject. For example, inventive nanoparticle compositions may be formulated in cosmetic or other preparations intended to be topically applies.

Human skin comprises the dermis and the epidermis. The epidermis has several layers of tissue, namely, stratum corneum, stratum lucidum, stratum granulosum, stratum spinosum, and stratum basale (identified in order from the outer surface of the skin inward). The stratum corneum presents the most significant hurdle in transdermal delivery of medications generally, and presumably of unmodified peptides in particular. The stratum corneum is typically about 10-15 µm thick, and it consists of flattened, keratised cells (corneocytes) arranged in several layers. The intercellular space between the corneocytes is filled with lipidic structures, and may play an important role in the permeation of substances through skin (Bauerova et al., 2001, *European Journal of Drug Metabolism and Pharmacokinetics*, 26:85; incorporated herein by reference).

The rest of the epidermis below the stratum corneum is approximately 150 µm thick. The dermis is about 1 mm-2 mm thick and is located below the epidermis. The dermis is innervated by various capillaries as well as neuronal processes.

Traditionally, attempts at transdermal administration of medication have been focused in increasing the permeability of the stratum corneum. Some attempts have included using chemical enhancing agents that increase the permeability of molecules through the skin. Some attempts have included using mechanical apparatus to bypass or ablate portions of the stratum corneum. In addition, attempts have included use of ultrasound or iontophoresis to facilitate the permeation of pharmaceuticals through the skin. In most cases, the goal has been to a pharmaceutical agent, typically a small molecule, through the skin, typically so that an agent may pass to the capillary bed in the dermis where the agent may be systemically incorporated into the subject to achieve a therapeutic effect.

The present invention provides, among other things, methods of administering unmodified peptides transdermally that do not require use of abrasive or other disrupting agents (whether chemical, mechanical, electrical, magnetic, etc.). Rather, the present inventors have surprisingly found that botulinum toxin incorporated into inventive nanoparticle compositions is effectively delivered transdermally without further steps to permeabilize or disrupt the stratum corneum. Use of such agents or steps with inventive botulinum nanoparticle compositions is not necessarily precluded in all embodiments of the present invention, but also is not required.

The present invention therefore provides methods of administering unmodified peptides through the topical application of an inventive nanoparticle composition. In some embodiments, the inventive nanoparticle composition is applied directly to the skin and for absorption through the epidermal layers. In some embodiments, the nanoparticle composition can penetrate the top layer of the skin, including the stratum corneum, dermal pores, and/or dermal glands, without the use of chemical or mechanical skin permeation enhancers or other agents that cause abrasion.

It will be appreciated by those of ordinary skill in the art that inventive compositions for topical administration may be prepared as a cosmetic formulation such as skin softener, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, or dermatological composition such as lotions, ointments, gels, creams, patches or sprays.

Such formulation of inventive nanoparticle compositions typically includes combination with one or more excipients such as, for example, fillers, sequestering agents, softeners, coloring materials (e.g. pigments and dyes), and fragrances.

In some embodiments, inventive nanoparticle compositions are formulated as a cream. The term "cream" refers to a spreadable composition, typically formulated for application to the skin. Creams typically contain an oil and/or fatty acid based-matrix. Creams formulated according to the present invention may contain nanoparticles and may be capable of substantially complete penetration (e.g., of such nanoparticles) through the skin upon topical administration. Such a cream could also act as a carrier for incorporated materials (e.g., for example, for a botulinum toxin).

Those of ordinary skill in the art will appreciate that inventive nanoparticle compositions may be incorporated into a device such as, for example, a patch.

A variety of transdermal patch structures are known in the art; those of ordinary skill will appreciate that inventive nanoparticle compositions may readily be incorporated into any of a variety of such structures. In some embodiments, a transdermal patch may further comprise a plurality of needles extending from one side of the patch that is applied to the skin, wherein the needles extend from the patch to project through the stratum corneum of the skin. In some embodiments, the needles do not rupture a blood vessel.

In some embodiments of the present invention, a nanoparticle composition can be provided in a depot in a patch so that pressure applied to the patch causes unmodified peptide to be directed out of the patch (optionally through needles) and through the stratum corneum.

In some embodiments of the present invention, a transdermal patch includes an adhesive. Some examples of adhesive patches are well known (for example, see U.S. Pat. Des. 296,006; U.S. Pat. Nos. 6,010,715; 5,591,767; 5,008,110; 5,683,712; 5,948,433; and 5,965,154; all of which are incorporated herein by reference). Adhesive patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

Those of ordinary skill in the art will appreciate that a transdermal patch is but one example of a device with which inventive nanoparticle compositions may be administered. To give but a few other examples, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes may be accomplished by filling the syringe with the composition. The composition may then be topically spread by the spatulas or swabs, or may be expelled from the syringes onto the person's skin.

In many embodiments of the invention, it may be desirable to limit delivery of unmodified peptides to only an intended delivery area. In some embodiments, such limited delivery may be accomplished by utilizing an inventive nanoparticle composition in an application device that permits application of the composition to a target site on the skin without applying the composition to non-target site areas of the skin. Clearly, a transdermal patch may be utilized to this end. Alternatively or additionally, if modified peptides are to be applied topically to only a selected area, other areas may be covered or pre-treated or otherwise protected from exposure.

EXEMPLIFICATION

The following examples are only intended to provide illustrations of specific embodiments contemplated by the present invention. The examples are not intended in any way to be limiting.

Example 1

Pentapeptide Nanoparticle Formulation

This example presents peptide nanoparticle compositions comprising a nanoemulsion containing a pentapeptide, KTTKS (SEQ ID NO.: 1), that is known to have biological activity on the skin structures (Katayama et al., supra).

A pentapeptide nanoemulsion preparation was prepared as follows:

800 mg of soybean oil and 800 mg of Tween 80 were stirred in a sterile vial for 5 minutes;

8.4 ml water with 0.0001 g of the peptide KTTTS (SEQ ID NO.: 1) was added and stirred for 20 minutes;

The sample was homogenized for 1 minute;

The sample was stirred for 20 minutes; and

The sample was microfluidized once at 23,000 psi.

The resulting pentapeptide nanoemulsion was evaluated for particle size using the Malvern Nano S particle sizer capable of sizing particles between about 0.6 nm-6000 nm. The pentapeptide nanoemulsion preparation had two particle size peaks having an average particle size of 106 nm (Table 2).

TABLE 2

Particle Size Distribution of a Pentapeptide Nanoparticle

| Size Range | Percent of Particles |
|---|---|
| 10-20 nm | 1.3% |
| 21-100 nm | 30.2% |
| 101-120 nm | 10.4% |
| 121-150 nm | 22.4% |
| 151-200 nm | 19.3% |
| 201-300 nm | 14.7% |
| 301-400 nm | 1.7% |
| Total | 100.0% |

Example 2

Pentapeptide Nanoparticle Formulation and Transdermal Penetration with Biological Effect This example presents peptide nanoparticles comprising a nanoemulsion containing a pentapeptide, KTTKS (SEQ ID NO.: 1), that is known to have biological activity on the skin structures (Katayama et al., supra; incorporated herein by reference). This example demonstrates the biological efficacy on the skin of transdermally applying a peptide nanoparticle, in this case KTTKS (SEQ ID NO.: 1).

Materials and Methods A pentapeptide nanoemulsion preparation was prepared as follows:

5.6 g of Labrafac WL 1349 oil and 5.6 g of Tween 80 were stirred in a sterile beaker for 5 minutes;

58.8 g Reagent Grade water was placed in a separate beaker; 0.010 g of the peptide KTTTS (SEQ ID NO.: 1) was added into the water and stirred for 20 minutes;

The contents of the first beaker were added to the contents of the beaker (i.e., the water and peptide) and then stirred for 20 minutes; and The entire sample was microfluidized once at 23,000 psi.

The resulting pentapeptide nanoemulsion was evaluated for particle size using the Malvern Nano S particle sizer capable of sizing particles between about 0.6 nm-about 6000 nm. The pentapeptide nanoemulsion preparation had an average particle size of 114.4 nm. Approximately 95% of the particles were below 130 nm in size.

The pentapeptide nanoemulsion was then mixed with an equal volume of a skin cream, (Base PCCA Vanishing Cream Light) and then vortexed into a uniform cream to yield the "Treatment Cream."

A "Control Cream" was prepared by the same method as the Treatment Cream, except that no peptide was added in the process.

Ten Swiss Webster mice were purchased that were each approximately 20 grams of weight. Upon arrival, all animals were acclimated to their cages for one week (group housed 5 mice per cage per group as defined below) and provided with standard cage bedding and Purina 5001 chow. After one week, the following treatment paradigms were applied:

Treatment Paradigms

Group 1 (Control): Each day for eight weeks, 5 mice each had 75 µl of the Control Cream applied to their backs with a gloved finger until no cream was visible. The mice had their backs shaved with an electric shaver two days prior to the first treatment and, thereafter, in one week intervals.

Group 2 (Treatment): Each day for eight weeks, 5 mice each had 75 µl of the Treatment Cream applied to their backs with a gloved finger until no cream was visible. The mice had their backs shaved with an electric shaver two days prior to the first treatment and, thereafter in one week intervals.

Assessment

The skin from the each mouse's back that was treated with either the Control or Treatment Cream was preserved and then processed with Masson's Trichrome histologic stain. The intensity of the staining was evaluated at a magnification of 400× using on a histologic scale of 1 to 4 for staining intensity: 1=almost no staining, collagen fibrils were very thin, 2=minimal staining and minimal collagen fibril width, 3=moderate staining and moderate fibril width, and 4=intense staining and wide fibrils.

Results

Histological Assessment

The average histologic score of the skin tissue stained with Masson's Trichrome stain was 2.33 out of a possible 4 in the Control Group. By comparison, the average histologic score of the stained skin of the mice in the Treatment Group was 3.67 out of a possible 4. This represents a 57% increase in collagen-staining intensity of the Treatment group over the Control Group. See FIG. 1 for examples of photomicrographs of skin tissue specimens from each of the Control and Treatment Groups.

Assessment of Skin Thickness Effects

The thickness of skin thickness is measured using a Skin Layer Thickness Test to determine the depth (in mm) of each skin layer following examination of a histologic cross-section of the mouse back skin that was microtomed and placed on a glass slide.

Assessment of Extracellular Matrix Production

Collagen is a major component of the content of the ExtraCellular Matrix. Collagen content is assessed using two separate histologic stains (Picro Sirius Red and Pterocarpus Osun) for collagen in two separate tests of mouse back skin that had microtomed and placed on a glass slide.

Collagen content is assessed by using the Western Blot technique to detect the hydroxyproline content of a homogenized preparation of the mouse's back skin. Hydroxyproline content is representative of collagen content.

Conclusion

The result show that, on average, the Treatment Group had statistically more collagen than the Control Group by histologic assessment. These controlled data show that the topical pentapeptide nanoemulsion preparation had a measurable biological effect on the skin when compared to a control cream without such a pentapeptide. Prior studies have shown that the peptide cannot penetrate the intact skin without chemical modification (Katayama et al., supra). Therefore, these data show that the inventive nanoemulsion formulation enabled penetration of unmodified peptide, resulting in effects to the skin consistent with the known biological action of the peptide in increasing collagen production in the skin and resultant increase in skin thickness.

The results are expected to show that, on average, the Treatment Group does have statistically thicker skin than the Control Group. The results are expected to show that, on average, the Treatment Group does have statistically more collagen than the Control Group and as measured by the two histologic stains and Western Blot measurement of hydroxyproline.

Example 3

Skin Thickening and Extra-Cellular-Matrix Stimulator Effects on Mice Through Transdermal Application of a Peptide Nanoparticle: Effect of Varying Concentration of Peptide in the Nanoparticle This example demonstrates the impact of varying the concentration of peptide in the nanoparticle on the biological efficacy on the skin of transdermally applying a peptide nanoparticle.

Materials and Methods

The experiment described Example 3 is repeated, except that the concentration of peptide in the Treatment cream is decreased by a factor of ten or increased by a factor of ten.

Results and Conclusion

The results are expected to show that, on average, those mice treated with the peptide concentration increased by a factor of ten have statistically thicker skin those mice treated with the increased peptide concentration. The results are expected to show that, on average, those mice treated with the peptide concentration increased by a factor of ten have statistically more collagen than those with decreased peptide concentration as measured by the two histologic stains and Western Blot measurement of hydroxyproline. In sum, these controlled data are expected to suggest that biological effect on the skin of the peptide nanoemulsion varies depending on the concentration of peptide incorporated.

Example 4

Administration of Pentapeptide Nanoparticle to Human Subjects to Reduce Skin Lines This example demonstrates the biological efficacy on the human skin of transdermally applying a peptide nanoparticle.

Materials and Methods

A pentapeptide nanoemulsion prepared in accordance with Example 1 or 2 is prepared and mixed with an equal volume of a skin cream, (Base PCCA Vanishing Cream Light) and then vortexed into a uniform cream to yield the "Treatment Cream."

A "Non-Nano Treatment Cream" is prepared by creating mixing the same amount of pentapeptide into the same amount of water as Example 1 and then vortexing with the same amount of skin cream as was used to prepare the Treatment Cream.

A "Control Cream" is prepared by vortexing the same amount of water as Example 1 or 2 and with the same amount of skin cream as was used to prepare the Treatment Cream.

Thirty healthy human subjects with prominent facial lines (such as observed in people with photo-damaged skin) are enrolled in a double-blind, placebo-controlled, split-faced study with left-right randomization. All subjects are graded with a five point scale by an observer blinded to treatment status. Score 0 of the scale is normal skin with a score of 5 being severe facial lines and wrinkles (primarily in the periocular or "crow's feet" area). Cheek skin texture is also assessed in terms of pore size (small to large) and smoothness (smooth to rough/pebbly). Subjects are only enrolled if they have a score on initial examination of 2.5 or greater. The face of the subjects will be photographed using standardized views and distances and lighting conditions.

Treatment Paradigms

The patient agrees not to use any facial skin care products for 3 weeks except for a Control Cream they can use twice daily at 12 hour intervals. After this initial "wash-out" period, each patient is given two tubes of cream marked "Right" and "Left" with a unique numerical code for each tube. They are instructed to use the Right Tube on the right side of the face and the Left Tube on the left side of the face twice daily at 12 hour intervals. They are instructed to apply a "pea-sized" amount of cream (approximately 0.4 g) to each side of the face. They are also instructed not to use other facial skin care products. For 10 of the subjects (the Control Group), the Right Tube contains the Control Cream and the Left Tube contains the Control Cream. For 10 of the subjects (the Non-Nano Treatment Group), the Right Tube contains the Control Cream and the Left Tube contains the Non-Nano Treatment Cream. For 10 of the subjects (the Nano Treatment Group), the Right Tube contains the Control Cream and the Left Tube contains the Nano Treatment Cream.

Assessment

The subjects are observed and photographed at 4, 8, and 12 weeks after beginning the treatment protocols following the wash-out period. In addition, an observer blinded to treatment status of the subject as well as the subject herself scores skin texture with the aforementioned scale for each of the right and left sides of the face.

Results and Conclusion

The results are expected to show that, on average, the Nano Treatment Group has statistically greater differences between the Right and Left facial texture scores (showing skin appearance improvement) than the differences observed between Right and Left scores for the Control Group and that the Non-Nano Treatment Group. In sum, these controlled data are expected to show that the topical pentapeptide nanoemulsion preparation has a measurable cosmetic effect on the skin when compared to a control cream without such a pentapeptide and a simple cream (Non-Nano Cream) with the same pentapeptide that was not in a nanoparticle formulation.

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any peptide, any peptide modification, any nanoparticle, any nanoemulsion, any surfactant, any oil, any premix component, any method of preparing nanoemulsions, any method of treatment, etc.), can be excluded from any one or more claims. For purposes of brevity, all of the embodiments in which one or more elements, features, purposes, or aspects is excluded are not set forth explicitly herein.

We claim:

1. An oil-in-water or water-in-oil dispersion comprising a population of particles, wherein the majority of particles have diameters between approximately 10 and approximately 300 nanometers;
   wherein the particles have an average particle size ranging between 50 nanometers and about 250 nanometers; and
   wherein said nanoparticles comprise at least one unmodified peptide of length between 2 and 30 amino acids that has biological activity in the skin, subcutaneous tissue or contiguous muscles.

2. The dispersion of claim 1, wherein the majority of particles have a range of diameters between approximately 10 and approximately 250 nanometers.

3. The dispersion of claim 1, wherein the majority of particles have a range of diameters between approximately 10 and approximately 200 nanometers.

4. The dispersion of claim 1, wherein the majority of particles have a range of diameters between approximately 10 and approximately 150 nanometers.

5. The dispersion of claim 1, wherein the majority of particles have a range of diameters between approximately 10 and approximately 120 nanometers.

6. The dispersion of claim 1, wherein the majority of particles have a range of diameters between approximately 10 and approximately 100 nanometers.

7. The dispersion of claim 1, wherein the majority of particles have a range of diameters between approximately 10 and approximately 50 nanometers.

8. The dispersion of claim 1, wherein said nanoparticles comprise an unmodified peptide whose amino acid sequence comprises KTTKS (SEQ ID NO: 1).

9. The dispersion of claim 1 wherein the amino acid sequence is selected from the group consisting of EYKTTKSSRL (SEQ ID NO: 2), GKTVIEYKTTKS (SEQ ID NO: 5), GKTVIEYKTTKSSRL (SEQ ID NO: 6), WGKTVIEYKTTKSSRLPIID (SEQ ID NO: 7), CTSHTGAWGKTVIEYKTTKS (SEQ ID NO: 8), and any combination thereof.

10. The dispersion of claim 1, wherein said nanoparticles comprise an unmodified peptide whose amino acid sequence comprises EYKTTKSSRL (SEQ ID NO: 2).

11. The dispersion of claim 1, wherein said nanoparticles comprise an unmodified peptide whose amino acid sequence comprises VIEYKTTK (SEQ ID NO: 3).

12. The dispersion of claim 1, wherein said nanoparticles comprise an unmodified peptide whose amino acid sequence comprises KTTK (SEQ ID NO: 4).

13. The dispersion of claim 1, wherein said nanoparticles comprise an unmodified peptide whose amino acid sequence comprises GKTVIEYKTTKS (SEQ ID NO: 5).

14. The dispersion of claim 1, wherein said nanoparticles comprise an unmodified peptide whose amino acid sequence comprises GKTVIEYKTTKSSRL (SEQ ID NO: 6).

15. The dispersion of claim 1, wherein said nanoparticles comprise an unmodified peptide whose amino acid sequence comprises WGKTVIEYKTTKSSRLPIID (SEQ ID NO: 7).

16. The dispersion of claim 1 wherein said nanoparticles comprise an unmodified peptide whose amino acid sequence comprises CTSHTGAWGKTVIEYKTTKS (SEQ ID NO: 8).

17. The dispersion of claim 1, wherein said nanoparticles comprise an unmodified peptide whose amino acid sequence comprises TTKS (SEQ ID NO: 9).

18. The dispersion of claim 1, wherein said nanoparticles comprise an unmodified peptide whose amino acid sequence comprises EEMQRR (SEQ ID NO: 10).

19. The dispersion of claim 1, wherein said nanoparticles comprise an unmodified peptide whose amino acid sequence comprises gastrin-releasing peptide.

20. The dispersion of claim 1, wherein said nanoparticles comprise an unmodified peptide whose amino acid sequence comprises VGVAPG (SEQ ID NO: 11).

21. The dispersion of claim 1, wherein said nanoparticles comprise an unmodified peptide whose amino acid sequence comprises YYRADA (SEQ ID NO: 12).

22. The dispersion of claim 1, wherein said nanoparticles comprise an unmodified peptide whose amino acid sequence comprises GHK (SEQ ID NO: 13).

23. The dispersion of claim 1, wherein said nanoparticles comprise an unmodified peptide whose amino acid sequence comprises TSLDASIIWAMMQN (SEQ ID NO: 14).

24. The dispersion of claim 1, wherein said nanoparticles comprise an unmodified peptide whose amino acid sequence comprises interferon.

25. The dispersion of claim 1, wherein said nanoparticles comprise an unmodified peptide whose amino acid sequence comprises interferon inducer.

26. The dispersion of claim 1 wherein said nanoparticles comprise an unmodified peptide whose amino acid sequence comprises P144.

27. The dispersion of claim 1, wherein the nanoparticle is a nanoemulsion.

28. The dispersion of claim 27, wherein the nanoemulsion comprises at least one oil, at least one surfactant, water, and the unmodified peptide.

29. The dispersion of claim 27, wherein the nanoemulsion comprises a single oil, a single surfactant, water, and the unmodified peptide.

30. The dispersion of claim 1, further comprising an oil, and wherein the oil is selected from the group consisting of almond oil, apricot oil, kernel oil, avocado oil, babassu oil, bergamot oil, black current seed oil, borage oil, cade oil, camomile oil, canola oil, caraway oil, carnauba oil, castor oil, cinnamon oil, cocoa butter, coconut oil, cod liver oil, coffee oil, corn oil, cotton seed oil, emu oil, eucalyptus oil, evening primrose oil, fish oil, flaxseed oil, geraniol oil, gourd oil, grape seed oil, hazel nut oil, hyssop oil, jojoba oil, kukui nut oil, lavandin oil, lavender oil, lemon oil, litsea cubeba oil, macademia nut oil, mallow oil, mango seed oil, meadowfoam seed oil, mink oil, nutmeg oil, olive oil, orange oil, orange roughy oil, palm oil, palm kernel oil, peach kernel oil, peanut oil poppy seed oil, pumpkin seed oil, rapeseed oil, rice bran oil, rosemary oil, safflower oil, sandalwood oil, sasquana oil, savoury oil, sea buckthorn oil, sesame oil, shea butter, soybean oil, sunflower oil, tea tree oil, thistle oil, tsubaki oil, vetiver oil, walnut oil, wheat germ oil; butyl stearate; caprylic triglyceride; capric triglyceride; cyclomethicone; diethyl sebacate; dimethicone 360; isopropyl myristate; mineral oil; octyldodecanol; oleyl alcohol; silicone oil; short chain triglycerides; medium chain triglycerides; long chain triglycerides; saturated oils thereof; and unsaturated oils thereof.

31. The dispersion of claim 30, wherein the oil is soybean oil.

32. The dispersion of claim 30, wherein the oil is a medium chain triglyceride.

33. The dispersion of claim 1, further comprising a surfactant, wherein the surfactant is selected from the group consisting of phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols; polyethylene glycol (PEG); polyoxyethylene-9-lauryl ether; a surface active fatty acid; palmitic acid; oleic acid; fatty acids; fatty acid monoglycerides; fatty acid diglycerides; fatty acid amides; sorbitan trioleate; glycocholate; sorbitan monolaurate; polysorbate 20; polysorbate 60; polysorbate 65; polysorbate 80; polysorbate 85; polyoxyethylene monostearate; surfactin; a poloxomer; a sorbitan fatty acid ester; sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipids; synthetic detergents having high surfactant properties; natural detergents having high surfactant properties; deoxycholates; cyclodextrins; chaotropic salts; and ion pairing agents.

34. The dispersion of claim 33, wherein the surfactant is a polysorbate.

35. The dispersion of claim 1, further comprising an oil and a surfactant, wherein the ratio of surfactant to oil ranges between 0.5:1 and approximately 2:1 by weight.

36. The dispersion of claim 1, further comprising an oil and a surfactant, wherein the ratio of surfactant to oil is approximately 0.25:1 by weight.

37. The dispersion of claim 1, further comprising an oil and a surfactant, wherein the ratio of surfactant to oil is approximately 0.5:1 by weight.

38. The dispersion of claim 1, further comprising an oil and a surfactant, wherein the ratio of surfactant to oil is approximately 1:1 by weight.

39. The dispersion of claim 1, further comprising an oil and a surfactant, wherein the ratio of surfactant to oil is approximately 2:1 by weight.

40. The dispersion of claim 1, further comprising an oil and a surfactant, wherein the ratio of surfactant to oil is approximately 3:1 by weight.

41. The dispersion of claim 1, wherein the nanoparticle is a nanomicelle.

42. The dispersion of claim 1, further comprising at least one additional component that, together with the dispersion, creates a cream, oil, ointment, gel, spray, lipstick, or sunscreen.

43. A method, comprising steps of: providing a subject; and administering an amount of an oil-in-water or water-in-oil dispersion comprising a population of particles, wherein the majority of particles have diameters between approximately 10 and approximately 300 nanometers;
   wherein the particles have an average particle size ranging between 50 nanometers and about 250 nanometers; and
   wherein said nanoparticles comprise at least one unmodified peptide of length between 2 and 30 amino acids that has biological activity in the skin, subcutaneous tissue or contiguous muscles, to the subject's skin such that a cosmetic or therapeutic benefit is attained.

44. The method of claim 43, wherein the dispersion is administered to the subject's skin at effective to thicken the subject's skin or subcutaneous tissue.

45. The method of claim 43, wherein the step of providing a subject comprises providing a subject suffering from, susceptible to, or exhibiting at least one symptom of fine skin lines; and wherein the dispersion is administered to the subject's skin at effective to treat, alleviate, ameliorate, relieve, delay onset of, inhibit progression of, reduce severity of, or reduce incidence of the fine skin lines.

46. The method of claim 43, wherein the step of providing a subject comprises providing a subject suffering from, susceptible to, or exhibiting at least one symptom of facial wrinkles; and wherein the dispersion is administered to the subject's skin at effective to treat, alleviate, ameliorate, relieve, delay onset of, inhibit progression of, reduce severity of, or reduce incidence of facial wrinkles.

47. The method of claim 43, providing a subject; and wherein the dispersion is administered to the subject's skin at effective to improve the appearance of the subject's skin.

48. The method of claim 43, providing a subject; and wherein the dispersion is administered to the subject's skin at effective to maintain the appearance of the subject's skin.

49. The method of claim 43, wherein the step of providing a subject comprises providing a subject suffering from a wound; and wherein the dispersion is administered to the subject's skin at an amount effective to treat, alleviate, ameliorate, relieve, inhibit progression of, or reduce severity of the wound.

50. The method of claim 43, wherein the step of providing a subject comprises providing a subject suffering from, susceptible to, or exhibiting at least one symptom of hypertrophic scarring, keloids, localized sclerosis, systemic sclerosis, or other condition characterized by excess accumulation of the extracellular matrix; and wherein the dispersion is administered to the subject's skin at an amount effective to treat, alleviate, ameliorate, relieve, delay onset of, inhibit progression of, reduce severity of, or reduce incidence of the at least one symptom associated with hypertrophic scarring, keloids, localized sclerosis, systemic sclerosis, or other condition characterized by excess accumulation of the extracellular matrix.

51. The method of any claim 43, wherein the step of administering is performed by hand, with a gloved finger, with an unprotected finger, by a device, with an adhesive patch, with a spatula, with a swab, with a syringe without a needle, or with a device that permits application of the dispersion to a target site on the skin without applying the dispersion to non-target sites of the skin.

52. The method of claim 43, wherein at least 99% of the unmodified peptide permeates the skin.

53. The method of claim 43, wherein at least 95% of the unmodified peptide permeates the skin.

54. The method of claim 43, wherein at least 90% of the unmodified peptide permeates the skin.

55. The method of claim 43, wherein at least 75% of the unmodified peptide permeates the skin.

56. The method of claim 43, wherein at least 50% of the unmodified peptide permeates the skin.

57. The method of claim 43, wherein at least 25% of the unmodified peptide permeates the skin.

58. The method of claim 43, wherein at least 10% of the unmodified peptide permeates the skin.

59. The method of claim 43, wherein at least 1% of the unmodified peptide permeates the skin.

60. A method, comprising steps of:
   providing a premix comprising an oil, a surfactant, water, and an unmodified peptide; and subjecting the premix to high shear force or high pressure homogenization for a period of time and under conditions which achieve the dispersion of claim 1.

61. The method of claim 60, wherein the step of subjecting the premix to high shear force or high pressure homogenization is achieved by microfluidization.

62. The method of claim 60, wherein the ratio of oil and surfactant in the premix ranges between approximately 0.5:1 and approximately 2:1 by weight.

63. A method for identifying unmodified peptides that improve the appearance of skin, comprising steps of:
   providing: at least one sample of skin; and
   at least one dispersion, wherein the dispersion comprises at least one unmodified peptide;
   administering the dispersion to the sample of skin; and
   monitoring the effect of the dispersion on the appearance of the sample of skin relative to the effect of a control substance.

* * * * *

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: peptide that may promote extra-cellular matrix
      production

<400> SEQUENCE: 1

Lys Thr Thr Lys Ser
1               5

<210> SEQ ID NO 2
<211> LENGTH: 10
<212> TYPE: PRT
<213> ORGANISM: Artificial Sequence
<220> FEATURE:
<223> OTHER INFORMATION: peptide that may promote extra-cellular matrix
      production

<400> SEQUENCE: 2

Glu Tyr Lys Thr Thr Lys Ser Ser Arg Leu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: peptide that may promote extra-cellular matrix
      production

<400> SEQUENCE: 3

Val Ile Glu Tyr Lys Thr Thr Lys
1               5

<210> SEQ ID NO 4
<211> LENGTH: 4
<212> TYPE: PRT
<213> ORGANISM: Artificial Sequence
<220> FEATURE:
<223> OTHER INFORMATION: peptide that may promote extra-cellular matrix
      production
```

```
<400> SEQUENCE: 4

Lys Thr Thr Lys
1

<210> SEQ ID NO 5
<211> LENGTH: 12
<212> TYPE: PRT
<213> ORGANISM: Artificial Sequence
<220> FEATURE:
<223> OTHER INFORMATION: peptide that may promote extra-cellular matrix
      production

<400> SEQUENCE: 5

Gly Lys Thr Val Ile Glu Tyr Lys Thr Thr Lys Ser
1               5                   10

<210> SEQ ID NO 6
<211> LENGTH: 15
<212> TYPE: PRT
<213> ORGANISM: Artificial Sequence
<220> FEATURE:
<223> OTHER INFORMATION: peptide that may promote extra-cellular matrix
      production

<400> SEQUENCE: 6

Gly Lys Thr Val Ile Glu Tyr Lys Thr Thr Lys Ser Ser Arg Leu
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: peptide that may promote extra-cellular matrix
      production

<400> SEQUENCE: 7

Trp Gly Lys Thr Val Ile Glu Tyr Lys Thr Thr Lys Ser Ser Arg Leu
1               5                   10                  15

Pro Ile Ile Asp
            20

<210> SEQ ID NO 8
<211> LENGTH: 20
<212> TYPE: PRT
<213> ORGANISM: Artificial Sequence
<220> FEATURE:
<223> OTHER INFORMATION: peptide that may promote extra-cellular matrix
      production

<400> SEQUENCE: 8

Cys Thr Ser His Thr Gly Ala Trp Gly Lys Thr Val Ile Glu Tyr Lys
1               5                   10                  15

Thr Thr Lys Ser
            20

<210> SEQ ID NO 9
<211> LENGTH: 4
<212> TYPE: PRT
<213> ORGANISM: Artificial Sequence
<220> FEATURE:
<223> OTHER INFORMATION: peptide that may promote extra-cellular matrix
      production

<400> SEQUENCE: 9

Thr Thr Lys Ser
```

```
<210> SEQ ID NO 10
<211> LENGTH: 6
<212> TYPE: PRT
<213> ORGANISM: Artificial Sequence
<220> FEATURE:
<223> OTHER INFORMATION: peptide that may decrease wrinkles

<400> SEQUENCE: 10

Glu Glu Met Gln Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: peptide that may improve wound healing

<400> SEQUENCE: 11

Val Gly Val Ala Pro Gly
1               5

<210> SEQ ID NO 12
<211> LENGTH: 6
<212> TYPE: PRT
<213> ORGANISM: Artificial Sequence
<220> FEATURE:
<223> OTHER INFORMATION: peptide that may improve wound healing

<400> SEQUENCE: 12

Tyr Tyr Arg Ala Asp Ala
1               5

<210> SEQ ID NO 13
<211> LENGTH: 3
<212> TYPE: PRT
<213> ORGANISM: Artificial Sequence
<220> FEATURE:
<223> OTHER INFORMATION: peptide that may improve wound healing

<400> SEQUENCE: 13

Gly His Lys
1

<210> SEQ ID NO 14
<211> LENGTH: 14
<212> TYPE: PRT
<213> ORGANISM: Artificial Sequence
<220> FEATURE:
<223> OTHER INFORMATION: eptide that may treat accumulation of excess
      extracellular matrix

<400> SEQUENCE: 14

Thr Ser Leu Asp Ala Ser Ile Ile Trp Ala Met Met Gln Asn
1               5                   10
```